United States Patent
Boije et al.

(10) Patent No.: US 6,750,252 B2
(45) Date of Patent: Jun. 15, 2004

(54) TRI-SUBSTITUTED PHENYL DERIVATIVES AND ANALOGUES

(75) Inventors: Maria Boije, Mölndal (SE); Jonas Fägerhag, Mölndal (SE); Eva-Lotte Lindstedt Alstermark, Mölndal (SE); Bengt Ohlsson, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/148,850

(22) PCT Filed: Nov. 29, 2000

(86) PCT No.: PCT/SE00/02385

§ 371 (c)(1),
(2), (4) Date: Nov. 13, 2002

(87) PCT Pub. No.: WO01/40172

PCT Pub. Date: Jul. 6, 2001

(65) Prior Publication Data

US 2003/0149104 A1 Aug. 7, 2003

(30) Foreign Application Priority Data

Dec. 3, 1999 (SE) .............................................. 9904421

(51) Int. Cl.[7] ...................... A61K 31/255; C07C 309/63
(52) U.S. Cl. ........................ 514/517; 558/52; 562/429
(58) Field of Search ................. 562/429; 514/517; 558/52

(56) References Cited

U.S. PATENT DOCUMENTS

| | | | |
|---|---|---|---|
| 6,258,850 B1 | 7/2001 | Andersson | 514/571 |
| 6,362,360 B1 | 3/2002 | Andersson et al. | 560/27 |

FOREIGN PATENT DOCUMENTS

| | | |
|---|---|---|
| WO | 9962870 | 12/1999 |
| WO | 9962871 | 12/1999 |
| WO | 9962872 | 12/1999 |

*Primary Examiner*—Rita Desai
*Assistant Examiner*—Golam M M Shameem
(74) *Attorney, Agent, or Firm*—White & Case LLP

(57) ABSTRACT

The present invention relates to certain tri-substituted phenyl derivatives and analogues of formula (I), to a process for preparing such compounds, having the utility in clinical conditions associated with insulin resistance, to methods for their therapeutic use and to pharmaceutical compositions containing them.

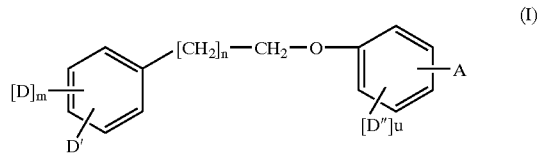

3 Claims, No Drawings

TRI-SUBSTITUTED PHENYL DERIVATIVES AND ANALOGUES

FIELD OF INVENTION

The present invention relates to certain tri-substituted phenyl derivatives and analogues, to a process for preparing such compounds, having the utility in clinical conditions associated with insulin resistance, to methods for their therapeutic use and to pharmaceutical compositions containing them.

BACKGROUND OF THE INVENTION

Insulin resistance, defined as reduced sensitivity to the actions of insulin in the whole body or individual tissues such as skeletal muscle, myocardium, fat and liver prevail in many individuals with or without diabetes mellitus. The insulin resistance syndrome, IRS, refers to a cluster of manifestations including insulin resistance with accompanying hyperinsulinemia, possibly type 2 diabetes mellitus, arterial hypertension, central (visceral) obesity, dyslipidemia observed as deranged lipoprotein levels typically characterised by elevated VLDL (very low density lipoproteins) and reduced HDL (high density lipoproteins) concentrations, the presence of small, dense LDL (Low Density Lipoprotein) particles and reduced fibrinolysis.

Recent epidemiological research has documented that individuals with insulin resistance run a greatly increased risk of cardiovascular morbidity and mortality, notably suffering from myocardial infarction and stroke. In non-insulin dependent diabetes mellitus these atherosclerosis related conditions cause up to 80% of all deaths. In clinical medicine there is at present only limited awareness of the need to increase the insulin sensitivity in IRS and thus to correct the dyslipidemia which is considered to cause the accelerated progress of atherosclerosis.

Furthermore there is at present no pharmacotherapy available to adequately correct the metabolic disorders associated with IRS. To date, the treatment of type 2 diabetes mellitus has been focused on correction of the deranged control of carbohydrate metabolism associated with the disease. Stimulation of endogenous insulin secretion by means of secretagogues, like sulphonylureas, and if necessary administration of exogenous insulin are methods frequently used to normalise blood sugar but that will, if anything, further enhance insulin resistance and will not correct the other manifestations of IRS nor reduce cardiovascular morbidity and mortality. In addition such treatment involves a significant risk of hypoglycaemia with associated complications.

Other therapeutic strategies have focused on aberrations in glucose metabolism or absorption, including biguanides, such as metformin, or glucosidase inhibitors, such as acarbose. Although these agents have been efficacious to a degree, their limited clinical effect is associated with side effects.

A novel therapeutic strategy involves the use of insulin sensitising agents, such as the thiazolidinediones which at least in part mediate their effects via an agonistic action on nuclear receptors. Ciglitazone is the prototype in this class. In animal models of IRS these compounds seem to correct insulin resistance and the associated hypertriglyceridaemia and hyperinsulinemia, as well as hyperglycaemia in diabetes, by improving insulin sensitivity via an effect on lipid transport and handling primarily in adipocytes, leading to enhanced insulin action in skeletal muscle, liver and adipose tissue.

Ciglitazone as well as later described thiazolidinediones in clinical development either have been discontinued reportedly due to unacceptable toxicity or show inadequate potency. Therefore there is a need for new and better compounds with insulin sensitising properties.

PRIOR ART

Compounds of the formula:

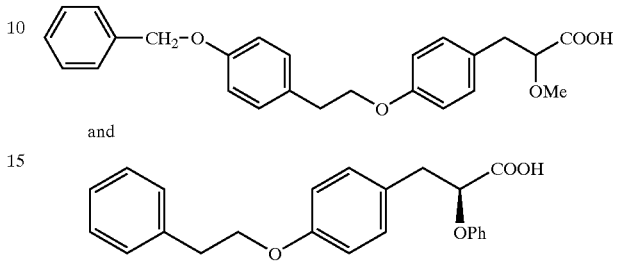

and and certain derivatives thereof disclosed in U.S. Pat. No. 5,306,726 and WO 91/19702 are said to be useful as hypoglycemic and hypocholesterolemic agents, and in U.S. Pat. No. 5,232,945 said to be useful in the treatment of hypertension.

AU 650 429 discloses structurally related compounds, but claimed to have different properties: diuretic, antihypertensive, platelets anti-aggregating and anti-lipoxygenase properties.

EP 139 421 discloses compounds having the ability to lower blood lipid and blood sugar levels. Among these compounds is troglitazone, a compound that has reached the market for treatment of NIDDM or decreased glucose tolerance. WO 97/31907 discloses compounds which are claimed to show good blood-glucose lowering activity and therefore to be of use in the treatment and/or prophylaxis or hyperglycaemia, dyslipidemia, and are of particular use in the treatment of Type II diabetes.

These compounds are also claimed to be of use for the treatment and/or prophylaxis of other diseases including Type I diabetes, hypertriglyceridemia, syndrome X, insulin resistance, heart failure, diabetic dyslipidemia, hyperlipidemia, hypercholesteremia, hypertension and cardiovascular disease, especially atherosclerosis.

EP0428423 discloses certain substituted 1-phenyl-2-phenoxy ethane compounds useful as anti-hypertensive or anti-platelet aggregation agents.

WO93/25521 discloses certain 1-substituted-4-(phenylmethyloxymethyl)benzene compounds as inhibitors of 12-lipoxygenase.

DESCRIPTION OF THE INVENTION

The invention relates to compounds of the general formula (I):

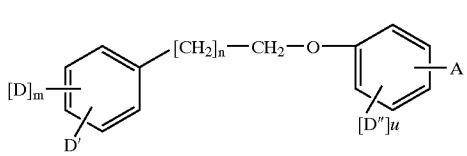

and stereo and optical isomers and racemates thereof as well as pharmaceutically acceptable salts, solvates and prodrug forms thereof, in which formula A is situated in the ortho, meta or para position and represents:

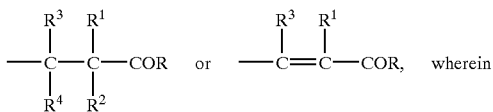

R is hydrogen;
- —OR$^a$, wherein R$^a$ represents hydrogen, alkyl, aryl or alkylaryl;
- —NR$^a$R$^b$, wherein R$^a$ and R$^b$ are the same or different and R$^a$ is as defined above and
- R$^b$ represents hydrogen, alkyl, aryl, alkylaryl, cyano, —OH, —Oalkyl, —Oaryl,
- —Oalkylaryl, —COR$^c$ or —SO$_2$R$^d$, wherein R$^c$ represents hydrogen, alky, aryl or alkylaryl and R$^d$ represents alkyl, aryl or alkylaryl;

R$^1$ is
- alkyl, aryl, alkene, alkyne, cyano;
- —OR$^e$, wherein R$^e$ is alkyl, acyl, aryl or alkylaryl;
- —O—[CH$_2$]$_p$—OR$^f$, wherein R$^f$ represents hydrogen, alkyl, acyl, aryl or alkylaryl and p represents an integer 1–8;
- —OCONR$^a$R$^c$, wherein R$^a$ and R$^c$ are as defined above;
- —SR$^d$, wherein R$^d$ is as defined above;
- —SO$_2$NR$^a$R$^f$, wherein R$^f$ and R$^a$ are as defined above;
- —SO$_2$OR$^a$, wherein R$^a$ is as defined above;
- —COOR$^d$, wherein R$^d$ is as defined above;

R$^2$ is hydrogen, halogen, alkyl, aryl, or alkylaryl,

R$^3$ and R$^4$ are the same or different and each represents hydrogen, alkyl, aryl, alkylaryl or halogen;

m is an integer 0–1, preferably m is 1;

n is an integer 1–6,

D is situated in the ortho, meta or para position and represents
- —OSO$_2$R$^d$, wherein R$^d$ is as defined above;
- —OCONR$^f$R$^a$, wherein R$^f$ and R$^a$ are as defined above;
- —NR$^c$COOR$^d$, wherein R$^c$ and R$^d$ are as defined above;
- —NR$^c$COR$^a$, wherein R$^c$ and R$^a$ are as defined above;
- —NR$^c$R$^d$, wherein R$^c$ and R$^d$ are as defined above;
- —NR$^c$SO$_2$R$^d$, wherein R$^c$ and R$^d$ are as defined above;
- —NR$^c$CONR$^a$R$^k$, wherein R$^a$, R$^c$ and R$^k$ are the same or different and each represents hydrogen, alkyl, aryl, or alkylaryl;
- —NR$^c$CSNR$^a$R$^k$, wherein R$^a$, R$^c$ and R$^k$ are the same or different and each represents hydrogen, alkyl, aryl or alkylaryl;
- —SO$_2$R$^d$, wherein R$^d$ is as defined above;
- —SOR$^d$, wherein R$^d$ is as defined above;
- —SR$^c$, wherein R$^c$ is as defined above;
- —SO$_2$NR$^a$R$^f$, wherein R$^f$ and R$^a$ are as defined above;
- —SO$_2$OR$^a$, wherein R$^a$ is as defined above;
- —CN,
- —CONR$^c$R$^a$, wherein R$^c$ and R$^a$ are as defined above;
- or alternatively D is —OR$^a$ wherein R$^a$ is defined above;

D' is situated in the ortho, meta or para position and represents hydrogen, alkyl, acyl, aryl, alkylaryl, halogen, —CN, —NO$_2$, —NR$^f$R$^b$, wherein R$^f$ and R$^b$ are as defined above;
- —OR$^f$, wherein R$^f$ is as defined above;
- —OSO$_2$R$^d$, wherein R$^d$ is as defined above; alternatively D' may represent cycloalkyl, CF$_3$, or aryl substituted by R$^f$;

D" is situated in the ortho, meta or para position (preferably D" is in the ortho position) each D" independently represents, alkyl, acyl, aryl, alkylaryl, halogen, —CN,
- —NR$^f$R$^b$ wherein R$^f$ and R$^b$ are as defined above;
- —OR$^f$, wherein R$^f$ is as defined above; and
- —OSO$_2$R$^d$, wherein R$^d$ is as defined above; and u is an integer 1 or 2.

For ease of reference the definitions of formula I above is henceforth referred to as defined in Category A. Unless otherwise stated the definitions of the various substituents are as defined under Category A throughout the present application.

For the avoidance of doubt D' is substituted in the ortho, meta or para position in relation to the —O— attached to the phenyl ring.

The compounds of formula I are surprisingly effective in conditions associated with insulin resistance.

Category A2: preferred compounds of the present invention are those of formula I, wherein A is situated in the meta or para position and represents,

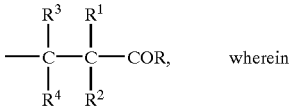

R is hydrogen;
- —OR$^a$, wherein R$^a$ is as defined in Category A;
- —NR$^a$R$^b$, wherein R$^a$ and R$^b$ are the same or different and R$^a$ is as defined in Category A and R$^b$ represents hydrogen, alkyl, aryl, alkylaryl, cyano, —OH, —Oalkyl or —Oalkylaryl;

R$^1$ is cyano;
- —OR$^d$, wherein R$^d$ is as defined in Category A;
- —O—[CH$_2$]p-OR$^a$, wherein p and R$^a$ are as defined in Category A;

R$^2$ is hydrogen or alkyl;

R$^3$ is hydrogen or alkyl;

R$^4$ is hydrogen;

n is an integer 1–3;

u is an integer 1 or 2;

m is an integer 0–1, preferably m is 1;

D is situated in the ortho, meta or para position and represents
- —OSO$_2$R$^d$, wherein R$^d$ is as defined in Category A;
- —OCONR$^a$R$^c$, wherein R$^a$ and R$^c$ are as defined in Category A;
- —NR$^c$COOR$^d$, wherein R$^c$ and R$^d$ dare as defined in Category A;
- —NR$^c$COR$^a$, wherein R$^c$ and R$^a$ are as defined in Category A;
- —NR$^c$R$^d$, wherein R$^c$ and R$^d$ are as defined in Category A;
- —NR$^c$SO$_2$R$^d$, wherein R$^c$ and R$^d$ are as defined in Category A;
- —NR$^c$CONR$^k$R$^c$, wherein R$^a$, R$^c$ and R$^k$ are as defined in Category A;
- —NR$^c$CSNR$^a$R$^k$, wherein R$^a$, R$^c$ and R$^k$ are as defined in Category A;
- —SO$_2$R$^d$, wherein R$^d$ is as defined in Category A;
- —CN;
- —CONR$^a$R$^c$, wherein R$^a$ and R$^c$ are as defined in Category A;
- or alternatively D is —OR$^a$ wherein R$^a$ is as defined in Category A;

D' is situated in the ortho, meta or para position and represents hydrogen, alkyl, alkylaryl, halogen, —CN or —NO$_2$;

—OR$^h$, wherein R$^h$ is hydrogen or alkyl;

D" is situated in the ortho or meta position (preferably D" is in the ortho position) and
represents alkyl, alkylaryl, halogen or —CN;
—OR$^h$, wherein R$^h$ is as defined above.

Category A3: further preferred compounds of the present invention are those within Category A2, wherein A is situated in the meta or para position;

R is —OR$^a$, wherein R$^a$ is hydrogen, alkyl or alkylaryl;
—NHR$^b$, wherein R$^b$ is hydrogen, alkyl, alkylaryl, cyano, —Oalkyl or —Oalkylaryl;

R$^1$ is —Oalkyl;

R$^2$ is hydrogen or alkyl;

R$^3$ is hydrogen or alkyl;

R$^4$ is hydrogen;

n is an integer 1–3;

u is an integer 1 or 2;

D is situated in the ortho, meta or para position and represents
—NR$^c$COOR$^d$, wherein R$^c$, and R$^d$ are as defined in Category A;
—OSO$_2$R$^d$, wherein R$^d$ is as defined in Category A;

D' is hydrogen;

D" is situated in the ortho or meta position (preferably D" is in the ortho position) and represents alkyl, alkyaryl, halogen or —CN.

Category A4: further preferred compounds of the present invention are those within Category A3, wherein A is situated in the para position;

R is —OH, —Oalkyl or —Oalkylaryl;
—NH$_2$, —NHOalkylaryl or —NHCN;

R$^1$ is —Oalkyl, preferably —Olower alkyl;

R$^2$ is hydrogen;

R$^3$ is hydrogen;

m is the integer 1;

n is the integer 1;

u is the integer 1;

D" is situated in the ortho position, and represents alkyl, alkylaryl, halogen or —CN.

Category A5: further preferred compounds of the present invention are those within Category A4, wherein D" is situated in the ortho position, and represents alkyl or alkylaryl.

Category A6: further preferred compounds of the present invention are those with Category A5, wherein D" is situated in the ortho position, and represent alkylaryl.

Category A7: further preferred compounds of the present invention are compounds which are one of the possible enantiomers.

"Pharmaceutically acceptable salt", where such salts are possible, includes both pharmaceutically acceptable acid and base addition salts. A suitable pharmaceutically-acceptable salt of a compound of Formula I is, for example, an acid-addition salt of a compound of Formula I which is sufficiently basic, for example an acid-addition salt with an inorganic or organic acid such as hydrochloric, hydrobromic, sulphuric, trifluoroacetic, citric or maleic acid; or, for example a salt of a compound of Formula I which is sufficiently acidic, for example an alkali or alkaline earth metal salt such as a sodium, calcium or magnesium salt, or an ammonium salt, or a salt with an organic base such as methylamine, dimethylamine, trimethylamine, piperidine, morpholine or tris-(2-hydroxyethyl)amine.

In vivo hydrolysable esters of the compounds of Formula I are just one type of prodrug of the parent molecule. Other prodrugs of the parent molecule are envisaged such as amide prodrugs, and can be prepared by routine methodology well within the capabilities of someone skilled in the art. Prodrugs of the compound of Formula I are within the scope of the invention. Various prodrugs are known in the art. For examples of such prodrug derivatives, see:

a) Design of Prodrugs, edited by H. Bundgaard, (Elsevier, 1985) and Methods in Enzymology. 42: 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p.113–191 (1991);

c) H. Bundgaard, Advanced Drug Delivery Reviews, 8:1–38 (1992);

d) H. Bundgaard, et al., Journal of Pharmaceutical Sciences, 77:285 (1988); and e) N. Kakeya, et al., Chem Pharm Bull, 32:692 (1984).

The preferred examples of prodrugs include in vivo hydrolysable esters of a compound of the Formula I. Suitable pharmaceutically-acceptable esters for carboxy include $C_{1-8}$alkyl esters, $C_{5-8}$cycloalkyl esters, cyclic amine esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxyC$_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl wherein alkyl, cycloalkyl and cyclicamino groups are optionally substituted by, for example, phenyl, heterocyclcyl, alkyl, amino, alkylamino, dialkylamino, hydroxy, alkoxy, aryloxy or benzyloxy, and may be formed at any carboxy group in the compounds of this invention.

It will also be understood that certain compounds of the present invention may exist in solvated, for example hydrated, as well as unsolvated forms. It is to be understood that the present invention encompasses all such solvated forms.

When the substituent OR$^a$ represents an alkylaryl group, the preferred alkylaryl is benzyl.

Throughout the specification and the appended claims, a given chemical formula or name shall encompass all stereo and optical isomers and racemates thereof as well as mixtures in different proportions of the separate enantiomers, where such isomers and enantiomers exist, as well as pharmaceutically acceptable salts thereof and solvates thereof such as for instance hydrates. Isomers may be separated using conventional techniques, e.g. chromatography or fractional crystallisation. The enantiomers may be isolated by separation of racemate for example by fractional crystallisation, resolution or HPLC. The diastereomers may be isolated by separation of isomer mixtures for instance by fractional crystallisation, HPLC or flash chromatography. Alternatively the stereoisomers may be made by chiral synthesis from chiral starting materials under conditions which will not cause racemisation or epimerisation, or by derivatisation, with a chiral reagent. All stereoisomers are included within the scope of the invention.

The following definitions shall apply throughout the specification and the appended claims.

Unless otherwise stated or indicated, the term "alkyl" denotes either a straight or branched alkyl group having from 1 to 6 carbon atoms or a cyclic alkyl atom having from 3 to 6 carbon atoms, the alkyl being substituted or unsubstituted. The term "lower alkyl" denotes either a straight or branched alkyl group having from 1 to 3 carbon atoms or a cyclic alkyl having 3 carbon atoms, the alkyl being substituted or unsubstituted. Examples of said alkyl and lower alkyl include methyl, ethyl, n-propyl, isopropyl, n-butyl, iso-butyl, sec-butyl, t-butyl and straight- and branched-chain pentyl and hexyl as well as cyclopropyl, cyclobutyl, cyclopentyl and cyclohexyl. Preferably alkyl is a substituted or unsubstituted straight or branched alkyl group having from 1 to 3 carbon atoms. Preferred alkyl groups methyl, ethyl, propyl, isopropyl and tertiary butyl.

Unless otherwise stated or indicated, the term "alkoxy" denotes a group O-alkyl, wherein alkyl is as defined above.

Unless otherwise stated or indicated, the term "halogen" shall mean fluorine, chlorine, bromine or iodine, preferably fluorine.

Unless otherwise stated or indicated, the term "aryl" denotes a substituted or unsubstituted phenyl, furyl, thienyl or pyridyl group, or a fused ring system of any of these groups, such as naphthyl.

Unless otherwise stated or indicated, the term "substituted" denotes an alkyl or an aryl group as defined above which is substituted by one or more alkyl, alkoxy, halogen, amino, thiol, nitro, hydroxy, acyl, aryl or cyano groups.

Unless otherwise stated or indicated, the term "alkylaryl" denotes a

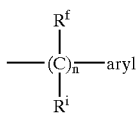

wherein n is an integer 1 to 6 and $R^f$ and $R^i$ are the same or different and each represents hydrogen or an alkyl or aryl group as defined above.

Unless otherwise stated or indicated, the term "acyl" denotes a group

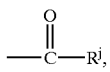

wherein $R^j$ is hydrogen, alkyl, alkoxy, aryl and alkylaryl as defined above.

Unless otherwise stated or indicated, the terms "alkenyl" and "alkynyl" denote a straight or branched, substituted or unsubstituted unsaturated hydrocarbon group having one or more double or triple bonds and having a maximum of 6 carbon atoms, preferably 3 carbon atoms.

Unless otherwise stated or indicated the term "protective group" ($R^p$) denotes a protecting group as described in the standard text "Protecting groups in Organic Synthesis", 2nd Edition (1991) by Greene and Wuts. The protective group may also be a polymer resin such as Wang resin or 2-chlorotrityl chloride resin.

Methods of Preparation

The compounds of the invention may be prepared as outlined below according to any of methods A–J. However, the invention is not limited to these methods, the compounds may also be prepared as described for structurally related compounds in the prior art.

A. The compounds of the invention of formula I wherein $R^2$ and $R^4$ are hydrogen can be prepared by a condensation reaction, such as a Knoevenagel or Wittig type reaction, of a carbonyl compound of the formula II:

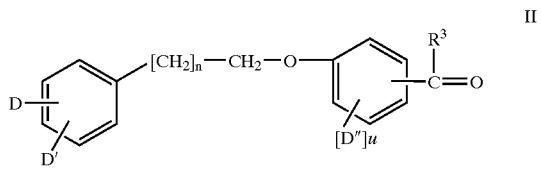

with a compound of the formula III or IV:

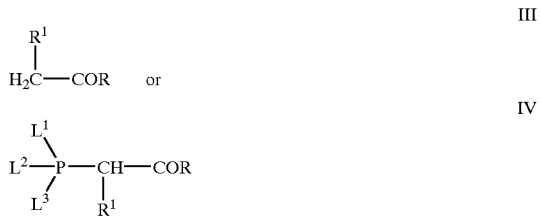

in which formulas D, D', D", u, n, R, $R^1$ and $R^3$ are as defined in Category A and $L^1=L^2=L^3$ are phenyl or $L^1=L^2$ are $OR^d$ (wherein $R^d$ is as defined in Category A) and $L^3$ is =O, and if desired, followed by reduction of the obtained double bond and removal of protective groups.

A1. In the condensation step approximately equimolar amounts of reactants are mixed in the presence of a base, such as sodium acetate, piperidine acetate, LDA or potassium tert-butoxide to provide the compound of formula I wherein A is the unsaturated moiety. This step may be carried out in the presence of an inert solvent or in the absence of solvent in which case the temperature should be sufficiently high to cause at least partial melting of the reaction mixture, a preferred such temperature is in the range of 100° C. to 250° C.

Sometimes it is necessary to add a dehydrating agent such as p-toluenesulfonic acid in order to achieve the formation of the double bond.

In a typical such reaction the aldehyde or ketone starting material and the compound of formula III are combined in approximately equimolar amounts and molar excess, preferably 1–5 fold, of anhydrous sodium acetate and the mixture is heated until it melts if necessary under vacuum. The compound of formula I wherein A is the unsaturated moiety, can then be isolated by mixing with water and acetone, followed by filtration of the formed precipitate. The crude product can be purified if desired, e.g. by recrystallisation or by standard chromatographic methods.

This reaction can also be performed conveniently in a solvent such as toluene in the presence of piperidine acetate. The reaction mixture is refluxed in a Dean-Stark apparatus to remove water. The solution is then cooled and the olefin product isolated and purified, by standard methods.

The reaction can also be performed by mixing the aldehyde or ketone and the compound of formula III in dry tetrahydrofuran, slowly adding potassium tert-butoxide at −20° C. and quenching the reaction with acetic acid. The crude product is isolated and then dissolved in toluene and refluxed with p-toluenesulfonic acid in an Dean-Stark apparatus to remove the water. The product is then isolated and purified, by standard methods.

A2. The reaction can also be performed in the presence of titanium (IV) chloride and pyridine in an inert solvent, such as chloroform.

A3. The condensation step could also be performed as a Wittig-type reaction (cf. Comprehensive Organic Synthesis vol. 1 p. 755–781 Pergamon Press) or as described in the experimental part.

Approximately equimolar amounts of reactants II and IV, are mixed in the presence of a base such as tetramethylguanidine or potassium carbonate in a 1–5 fold molar excess. This reaction may be carried out in the presence of an inert solvent such as dichloromethane or isopropanol at a suitable temperature (–10° C.–+60° C.) and at a time long enough.

The compound of the formula II is prepared by coupling a compound of the formula V:

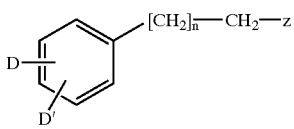

with a compound of the formula VI:

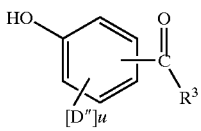

in which formulas D, D', D", u, n and $R^3$ are as defined in Category A, at, for example alkylation conditions or by a Mitsunobu reaction (Tsunoda, Tetr. Lett. 34, 1639–42 (1993), when necessary followed by modifications of the D-groups.

The group Z can be —OH or a leaving group, such as halogen, sulfonate or triflate.

The compounds of formula III, IV, V or VI are either commercially available or can be prepared by standard procedures known to anyone skilled in the art from commercially available starting materials.

The reduction of the olefin may be carried out by using a wide variety of reducing methods known to reduce carbon-carbon double bonds, such as catalytic hydrogenation in the presence of an appropriate catalyst, magnesium or sodium amalgam in a lower alcohol such as methanol, or hydrogen transfer reagents such as diethyl-2,5-dimethyl-1,4-dihydropyridine-3,5-dicarboxylate.

The catalytic hydrogenation can be conducted in alcohol, cellosolves, protic polar organic solvents, ethers, lower aliphatic acids, and particularly in methanol, ethanol, methoxyethanol, dimethylformamide, tetrahydrofuran, dioxane, dimetoxyethane, ethyl acetate or acetic acid, either used alone or in mixture. Examples of the catalyst used include palladium black, palladium on activated charcoal, platinum oxide or Wilkinson's catalyst. The reaction can proceed at different temperatures and pressures depending on the reactivity of the aimed reaction.

In case of hydrogen transfer reaction with diethyl-2,5-dimethyl-1,4-dihydropyridine-3,5-dicarboxylate, equimolar amounts of reactants are mixed and the mixture is warmed to melting (140° C.–250° C.) under inert atmosphere or under vacuum.

B. The compounds of the invention of formula I where A=—$CR^3R^4$—$CR^1R^2$—COR, wherein $R^4$ is hydrogen can be prepared by reacting a carbonyl compound of formula II C:

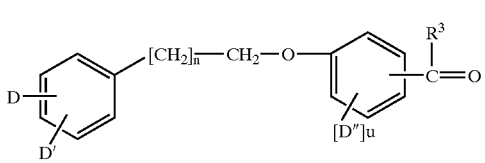

with a compound of formula VII:

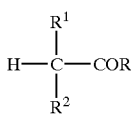

in which formulas D, D', D", u, n, $R^1$ and $R^3$ are as defined in Category A and $R^2$ is alkyl, aryl or alkylaryl, followed by dehydroxylation and if necessary by removal of protective groups.

In the reaction the compound of formula II is reacted with a compound of formula VII in the presence of a strong base such as LDA in an inert solvent followed by addition of a dehydroxylating agent such Suitable reaction conditions and reagents are described in Synthetic Communications Smonou I et al., (1988) 18, 833, and Synthesis Olag G. Et al., (1991) 407, and J. Heterocyclic Chemistry Georgiadis, M. P. Etal., (1991) 28(3), 599–604, and Synth. Commun. Majeticj, G. et al. (1993), 23(16), 2331–2335, and Bioorg. Med. Chem. Lett. (1998) 8(2), 175–178. The reaction can be carried out as described in the experimental section or by standard methods know to anyone skilled in the art.

The compound of formula VII are either commercially available or can be prepared by standard procedures.

C. The compounds of the invention of formula I where A=$CR^3R^4$—$CR^1R^2$—COR, can be prepared by an alkylation reaction with a compound of formula VIII:

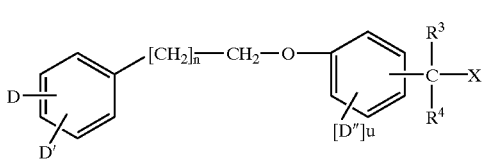

where in X is a leaving group, such as a halogen, sulfonate or triflate, on a compound of formula VII:

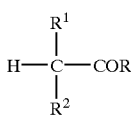

in which formulas D, D', D", m, n, R, $R^1$, $R^2$, $R^3$ and $R^4$ are as defined in Category A and, if desired, followed by removal of protective groups.

In the alkylation step the compound of formula VII is reacted with a compound of formula VIII in the presence of one or more bases such as potassium carbonate, triethylbenzylammonium chloride, sodium hydride, LDA, butyllithium or LHMDS and in a inert solvent such as acetonitrile, DMF or dichloromethane at a suitable temperature and time.

The reaction can be carried out as described in the examples or by standard methods known in the literature. (Synth. Comm. 19(788) 1167–1175 (1989)).

The compound of formula VIII can be prepared from an alcohol of formula IX:

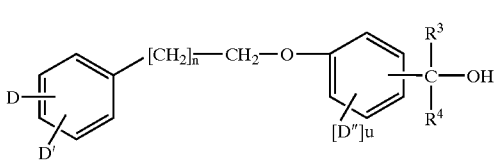

IX wherein D, D', D", u, n, $R^3$ and $R^4$ are as defined in Category A, using standard methods.

The compound of formula IX can be prepared from a compound of formula II either by reduction with a reducing agent known to convert a carbonyl group to a hydroxyl group such as lithium borohydride or sodium borohydride or by reaction with an organometallic compound such as an organolithium or a Grignard reagent by standard methods.

D. The compounds of the invention of formula I can be prepared by reaction of a compound of the formula:

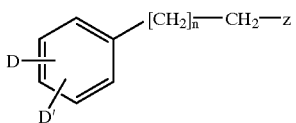

V with a compound of the formula X:

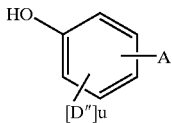

X in which formulas D, D', D", u, n and A are as defined in Category A, and Z is —OH or a leaving group such as halogen, sulfonate, triflate, either by an alkylation reaction or a Mitsunobu reaction, when necessary followed by removal of protective groups.

The compound of formula X can be prepared in accordance with methods described in A from a compound of formula III, in which the hydroxy group is protected (for example with a benzyl protecting group) and a compound of formula VI (wherein $R^3$ is hydrogen), followed by removal of the protecting group.

Compounds of formula VI, wherein $R^3$ is hydrogen, can be made by oxidation of a compound of formula VIa:

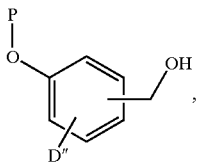

VIa in which formulas D" is as defined in Category A and P is a suitable protecting group. Any suitable oxidising reagent for the conversion of an alcohol to an aldehyde may be used, for example pyridinium chlorochromate.

Compounds of formula VIa may be formed by reducing the ester compound VIb to the alcohol VIa:

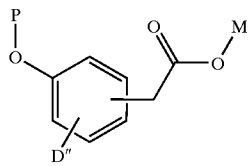

VIb wherein M is any group suitable for the formation of the ester to the alcohol. Any suitable reducing reagent, for the conversion of an ester to its alcohol may be used, for example $LiALH_4$. Compounds of formula VIb may be prepared from known starting materials and from routes described in the literature, such as J. Amer. Chem. Soc. (1974), 96, 2121–2129.

D1. In an alkylation reaction the leaving group $R^1$ can be a sulfonate such as mesylate, nosylate, tosylate, or a halogen, such as bromine or iodine. The compounds of formula V and X, in approximately equimolar amounts or with an excess of one of the compounds, are heated to reflux temperature in an inert solvent, such as isopropanol or acetonitrile, in the presence of a base, such as potassium carbonate or cesium carbonate.

The mixture is refluxed for the necessary time, typically between 0.5 h to 24 h, the work up procedure usually include filtration, for removal of solid salt, evaporation and extraction with water and an organic solvent such as dichloromethane, ethyl acetate, or diethyl ether.

The crude product is purified if desired e.g. by recrystallisation or by standard chromatographic methods.

D2. The Mitsunobu reaction can be carried out according to standard methods.

In a typical Mitsunobu reaction a compound of formula V, wherein the group $R^1$ is a hydroxyl group, and a compound of formula X are mixed, in approximately equimolar amounts or with an excess of one of the compounds, in an inert solvent, such as chloroform, dichloromethane, or tetrahydrofuran. A slight molar excess of an azodicarboxylate, (1–4 equivalents) such as DEAD or ADDP and a phosphine (1–4 equivalents), such as tributylphosphine or triphenylphosphine are added and the reaction mixture is stirred at a temperature high enough, for example room temperature, and a time long enough (1–24 hours) to obtain the crude product, which can be worked up according to standard literature methods and if desired purified, e.g. by standard chromatographic methods.

E. The compounds of the invention of formula I wherein A is —$CR^3R^4$—$CR^1R^2$—COR, wherein R, $R^2$, $R^3$ and $R^4$ are as defined in Category A and $R^1$ is
  —$OR^e$, wherein $R^e$ is as defined in Category A,
  —O—$[CH_2]_m$—$OR^f$, wherein m and $R^f$ are as defined in Category A,
  —$OCONR^aR^c$, wherein $R^a$ and $R^c$ are as defined in Category A,
can be prepared by converting a compound of formula XI:

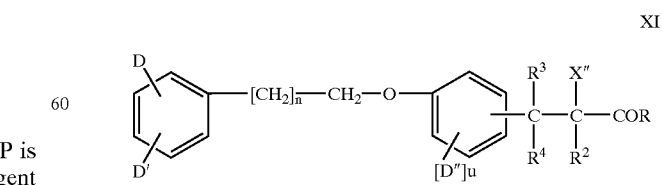

XI wherein D, D', D", u, n, R, $R^2$, $R^3$ and $R^4$ are as defined in Category A and X" is —OH followed, if necessary, by removal of protective groups.

The reaction may be carried out as an alkylating reaction, a Mitsunobu reaction, an esterfication reaction or by reaction with isocyanates. The alkylating reaction may be carried out using a variety of alkylating agents, such as alkyl halide. The esterfication reaction may be carried out using a variety of acylating agents such as Cl—CO—$R^d$ (wherein $R^d$ is as defined in Category A) and the Mitsunobu reaction may be carried out using an alcohol such as phenol. The reactions can be carried out in accordance with methods known to those skilled in the art.

The compound of formula XI can be prepared by reaction of a compound of formula V:

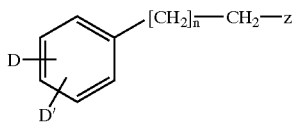

V with a compound of formula XII:

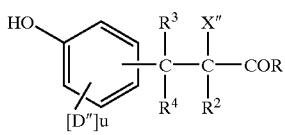

XII wherein D, D', D", u, n, R, $R^2$, $R^3$, $R^4$ are as defined in Category A and Z is —OH or a leaving group such as halogen, sulfonate or triflate and X" is —OH followed, if necessary, by removal of protective groups.

The reaction can be performed as described above or by standard methods know to anyone skilled in the art.

The compound of the formula XII can be prepared according to literature methods from commercially available starting materials.

F. The compounds of the formula I wherein A is —$CR^3R^4$—$CR^1R^2$—COR, and R, $R^2$, $R^3$ and $R^4$ are as defined in Category A and $R^1$ is —$SR^d$, wherein $R^d$ is as defined in Category A, can be prepared by reacting a compound of the formula XIII:

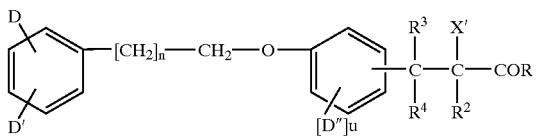

XIII wherein D, D', D", u, n, R, $R^2$, $R^3$, $R^4$ are as defined in Category A and X' is halogen, a thiol in a substitution reaction. The reaction can be carried out in accordance to methods known to those skilled in the art.

The compound of formula XIII can be prepared in accordance to method D from either commercially available starting materials or from starting materials prepared by standard procedures from commercially available starting materials.

G. The compounds of the invention of formula I wherein D is —$OSO_2R^d$, —$SR^c$, —$OCONR^fR^a$, —$NR^cCOOR^d$, —$NR^cCOR^a$, —$NR^cR^d$,
—$NR^cCONR^aR^k$, $NR^cSO_2R^d$ and
—$NR^cCSNR^aR^k$, wherein $R^a$, $R^c$, $R^d$, $R^f$ and $R^k$ are as defined in Category A, can be prepared by reacting a compound of formula XIV:

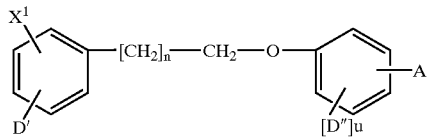

XIV wherein D', D", u, n and A are as defined in Category A and $X^1$=—OH, —SH or —$NR^cH$, with a suitable reagent, such as a sulfonylhalide, isocyanate, acylhalide, chloroformate, anhydride or an alkylhalide in an inert solvent such as dichloromethane or toluene and when necessary in the presence of a base, such as triethylamine or pyridine and eventually followed by removal of protective groups.

The reaction can be carried out in accordance with methods know to those skilled in the art or as described in the examples.

H. The compounds of the invention of formula I where R is —OH can be prepared from a compound of formula I where in R is —$OR^p$, wherein $R^p$ is a protective group such as alkyl, aryl, alkylaryl or a polymer resin such as Wang resin or 2-chlorotrityl chloride resin, by removal of the protective group by hydrolysis. The hydrolysis can be performed according to standard methods either under basic or acidic conditions.

I. The compound of the invention of formula I wherein R is —$NR^aR^b$ can be prepared by reacting a compound of formula I when R is —OH with a compound of formula HN$R^aR^b$ in the presence of a peptide coupling system (e.g. EDC, DCC, HBTU, TBTU or PyBop or oxalylchloride in DMF), an appropriate base (e.g. pyridine, DMAP, TEA or DIPEA) and a suitable organic solvent (e.g. dichloromethane, acetonitrile or DMF) in accordance to methods known to those skilled in the art or as described in the examples.

J. The compounds of the invention of formula I where D is —$SO_2R^d$ or —$SOR^d$, wherein $R^d$ is as defined in Category A, can be prepared by oxidizing a compound of formula XV:

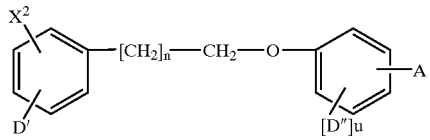

XV wherein D', D", u, n and A are as defined in Category A and $X^2$ is —$SOR^d$ or —$SR^d$, wherein $R^d$ is as defined in Category A with oxidizing agents such as m-chloroperoxybenzoic acid or hydrogen peroxide in an inert solvent such as dichloromethane eventually followed by removal of protective groups.The reactions can be carried out according to standard procedures.

The compounds of the invention may be isolated from their reaction mixtures using conventional techniques.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

In any of the preceding methods of preparation A–J, where necessary, hydroxy, amino or other reactive groups may be protected using a protecting group, $R^P$ as described in the standard text "Protective groups in Organic Synthesis", $2^{nd}$ Edition (1991) by Greene and Wuts. The protecting group $R^P$ may also be a resin, such as Wang resin or 2-chlorotrityl chloride resin. The protection and deprotection of functional groups may take place before or after any of the reaction steps described hereinbefore. Protecting groups may be removed in accordance to techniques which are well known to those skilled in the art.

The expression "inert solvent" refers to a solvent which does not react with the starting materials, reagents, intermediates or products in a manner which adversely affects the yield of the desired product.

Pharmaceutical Preparations

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient either as a free acid, or a pharmaceutical acceptable organic or inorganic base addition salt, in a pharmaceutically acceptable dosage form. Depending upon the disorder and patient to be treated and the route of administration, the compositions may be administered at varying doses.

The compounds of the invention may also be combined with other therapeutic agents which are useful in the treatment of disorders associated with the development and progress of atherosclerosis such as hypertension, hyperlipidemias, dyslipidemias, diabetes and obesity. Suitable daily doses of the compounds of the invention in therapeutic treatment of humans are about 0.001–10 mg/kg body weight, preferably 0.01–1 mg/kg body weight.

According to a further aspect of the invention there is thus provided a pharmaceutical formulation including any of the compounds of the invention, or pharmaceutically acceptable derivatives thereof, in admixture with pharmaceutically acceptable adjuvants, diluents and/or carriers.

Pharmacological Properties

The present compounds of formula (I) are useful for the prophylaxis and/or treatment of clinical conditions associated with reduced sensitivity to insulin (insulin resistance) and associated metabolic disorders. These clinical conditions will include, but will not be limited to, abdominal obesity, arterial hypertension, hyperinsulinaemia, hyperglycaemia, type 2 diabetes mellitus and the dyslipidaemia characteristically appearing with insulin resistance. This dyslipidaemia, also known as the atherogenic lipoprotein profile, phenotype B, is characterised by moderately elevated non-esterified fatty acids, elevated very low density lipoproteins (VLDL) triglyceride rich particles, low high density lipoproteins (HDL) particle levels cholesterol and the presence of small, dense, low density lipoprotein (LDL) particles. Treatment with the present compounds is expected to lower the cardiovascular morbidity and mortality associated with atherosclerosis. These cardiovascular disease conditions include macro-angiopathies causing myocardial infarction, cerebrovascular disease and peripheral arterial insufficiency of the lower extremities. Because of their insulin sensitising effect the compounds of formula I are also expected to prevent or delay the development of type 2 diabetes and thus reduce the progress of clinical conditions associated with chronic hyperglycaemia in diabetes type I such as the micro-angiopathies causing renal disease, retinal damage and peripheral vascular disease of the lower limbs. Furthermore the compounds may be useful in treatment of various conditions outside the cardiovascular system associated with insulin resistance like polycystic ovarian syndrome.

Working Examples $^1$H NMR and $^{13}$C NMR measurements were performed on a VARINA MERCURY 300 or Varian UNITY plus 400, 500 or 600 spectrometers, operating at $^1$H frequencies of 300, 400, 500 and 600 MHz, respectively, and at $^{13}$C frequencies of 75, 100, 125 and 150 MHz, respectively. Measurements were made on the delta ($\delta$) scale.

Unless otherwise stated, chemical shifts are given in ppm with the solvent as internal standard

| | |
|---|---|
| IRS | insulin resistance syndrome |
| LDA | lithium diisopropylamide |
| LHMDS | lithium hexamethyldisilylamine |
| DMF | dimethylformamide |
| DMAP | Dimethylaminopyridin |
| DEAD | diethyl azodicarboxylate |
| ADDP | azodicarbonyl dipiperidine |
| EDC | 1-(3-dimethylaminopropyl)-3-ethylcarbodiimide |
| DCC | dicyclohexylcarbodiimide |
| HBTU | O-benzotriazol-1-yl-N,N,N',N'-tetramethyluronium hexafluorophosphate |
| TBTU | O-benzotriazol-1-yl-N,N,N',N'-tetramethyluronium tetrafluoroborate |
| PyBop | benzotriazole-1-yl-oxy-tris-pyrolidino-phosphonium hexafluorophosphate |
| TEA | triethylamine |
| DIPEA | diisopropylethylamine |
| TLC | thin layer chromatography |
| THF | tetrahydrofuran |
| Pd/C | palladium on charcoal |
| HOBtxH$_2$O | 1-hydroxybeazotriazole-hydrate |
| DIBAH | diisobutylaluminium hydride |

EXAMPLE 1

3-[4-Benzyl-3-({4-[(methylsulfonyl)oxy]phenethyl}oxy)phenyl]-2-ethoxypropanoic acid Ethyl 3-[4-benzyl-3-({4-[(methylsulfonyl)oxy]phenethyl}oxy)phenyl]-2-ethoxypropanoate (0.48 g), LiOH (0.024 g), THF (10 ml), ethanol (2 ml) and water (2 ml) were added to a reaction flask. The solution was stirred 4 h at room temperature. Aqueous solution, 1 M, of potassium hydrogen sulfate (2 ml) was added to the reaction flask. The solvent was evaporated. The residue was extracted twice by ethyl acetate. The organic phase was dried by magnesium sulfate and filtered. The solvent was evaporated and the product isolated (0.4 g).

$^{13}$C-NMR(150 MHz, CDCl$_3$): 15.0, 35.2, 35.7, 37.2, 38.7, 65.8, 66.7, 68.2, 112.6, 121.6, 121.8, 425.7, 128.1, 128.2, 128.8, 130.3, 130.5, 136.2, 138.1, 140.9, 147.7, 156.1, 175.5

EXAMPLE 2

Ethyl 3-[4-benzyl-3-({4-[(methylsulfonyl)oxy]phenethyl}oxy)phenyl]-2-ethoxypropanoate Ethyl 3-(4-benzyl-3-hydroxyphenyl)-2-ethoxypropanoate (0.68 g), potassium carbonate (0.43 g), PEG 400 (0.40 g) and 2-butanone (25 ml) were added to a reaction flask. At reflux, 2-(4-methylsulfonyloxyphenyl)ethylmethanesulfonate(1.1 g) was added in small portions over 4 hours to the reaction mixture. The solvent was evaporated. The residue was divided between diethyl ether and water. The organic phase was washed with water and the solvent evaporated. The crude product was flash chromatographed with a mixture of diethyl ether-petroleum ether, gradient from 25–75 to 50–50 from which the product was isolated (0.5 g, yield 46%.

$^1$H-NMR(500 MHz, CDCl$_3$): 1.20 (t, 3H), 1.25 (t, 3H), 3.00 (m, 2H), 3.10 (m, 2H), 3.14 (s, 3H), 3.39 (m, 1H), 3.64 (m, 1H), 3.93 (s, 2H), 4.03 (m, 1H), 4.20 (m, 4H), 6.80 (m, 2H), 7.02 (d, 1H), 7.17 (m, 2H), 7.22 (m, 3H), 7.29 (m, 4H).

Starting Material (a) 2-(4-Methylsulfonyloxyphenyl)ethylmethanesulfonate

4-Hydroxyphenethyl alcohol (15 g; 0.108 mole) was dissolved in dichloromethane. Triethylamine (27.3 g; 0.27 mole) was added followed by addition of a solution of methanesulphonyl chloride (27.2 g; 0.239 mole) in dichloromethane at 0° C. The reaction mixture was allowed to reach room temperature, then stirred at room temperature and followed by TLC. The reaction mixture was filtered. The filtrate was washed with water, the phases were separated and the organic phase was dried with sodium sulfate and evaporated in vacuo to give 28 g (yield 88%) of the desired product.

$^1$H-NMR (400 MHz;CDCl$_3$): 2.85 (s, 3H), 3.05 (t, 2H), 3.15 (s, 3H), 4.35 (s, 2H), 7.2 (dm, 2H), 7.25 (dm, 2H).

$^{13}$C-NMR (100 MHz; CDCl$_3$): 34.8, 37.3, 69.6, 122.2, 130.5, 135.8, 148.1.

EXAMPLE 3

Isopropyl 3-[4-benzyl-3-({4-[(methylsulfonyl)oxy]phenethyl}oxy)phenyl]-2-ethoxypropanoate Isopropyl 3-(4-benzyl-3-hydroxyphenyl)-2-ethoxypropanoate (0.37 g), PEG 400 (0.25 g) and 2-butanone (5 ml) were added to a reaction vessel. At reflux 2-(4-methylsulfonyloxyphenyl)ethylmethanesulfonate(0.7 g) and potassium carbonate (0.44 g) were added in small portions to the reaction mixture over a 5 hour period. The reaction mixture was stirred for a further 1 hour at reflux. The solution was divided between water and diethyl ether. The organic phase was dried with sodium sulfate and filtered. The solvent was evaporated. Chromatography from diethyl ether and petroleum ether. Product isolated in an amount of 0.34 g, yield 58%.

Starting Material—Ethyl 3-(4-benzyl-3-hydroxyphenyl)-2-ethoxypropanoate

Ethyl (Z)-3-[4-benzyl-3-(benzyloxy)phenyl]-2-ethoxy-2-propenoate (2.1 g), palladium on charcoal (0.1 g) and ethyl acetate (100 ml) were added to a reaction flask. Hydrogenation reaction was carried out at 1 atm pressure one-night at room temperature. The crude product was filtered and the solvent evaporated. Chromatography of the crude material from diethyl ether and petroleum ether, gradient elution from 5–95 to 20–80 gave two fractions. Fraction 1 contained isopropyl 3-(4-benzyl-3-hydroxyphenyl)-2-ethoxypropanoate, 0.37 g. Fraction 2 contained the product in an amount of 0.67 g.

$^1$H-NMR(300 MHz, CDCl3): 1.18 (t, 3H), 1.22 (t, 3H), 2.96 (m, 2H), 3.39 (m, 1H), 3.62 (m, 1H), 3.96–4.05 (m, 3H), 4.18 (q, 2H), 6.70–6.80 (m, 2H), 7.03 (d, 1H), 7.17–7.34 (m, 5H).

(a) Ethyl (Z)-3-[4-benzyl-3-(benzyloxy)phenyl]-2-ethoxy-2-propenoate

Compound (b) (2.0 g), (1,2-diethoxy-2-oxoethyl)(triphenyl)phosphonium chloride (3.4 g), potassium carbonate (1.37 g) and isopropyl alcohol (60 ml) were added to a reaction vessel. The mixture was refluxed under a nitrogen atmosphere. The solid material was filtered off and the solvent evaporated. The crude product was dissolved in diethyl ether and washed with potassium hydrogen sulfate (1 M), twice. The etheral solution was dried with sodium sulfate and the solvent evaporated. Chromatography from diethyl ether and petroleum ether gave an isolated product containing several substances according to HPLC and 1H NMR. It was a mixture of cis and trans isomers and also some isopropyl ester compounds. Transesterification had occured with the solvent, isopropyl alcohol during the reaction. The crude product (2.1 g) was used as it was in the next reaction step, which was hydrogenation—see above Example 4.

$^1$H-NMR(500 MHz, CDCl3): 1.37 (t, 3H), 1.41 (t, 3H), 4.01 (q, 2H), 4.08 (s, 2H), 4.34 (q, 2H), 5.14 (s, 2H), 5.18 (s, 1H), 7.00 (s, 1H), 7.15 (d, 1H), 7.2–7.5 (m, 10H), 7.61 (s, 1H).

(b) 4-Benzyl-3-(benzyloxy)benzaldehyde

Pyridinium chlorochromate (5.3 g) was dissolved in methylene chloride (300 ml). A solution of compound (c) (5.0 g) in methylene chloride (25 ml) was added dropwise to the reaction. The solution was stirred for 3 hours at room temperature. Diethyl ether was added and the formed precipitate was filtered off. The solvent was evaporated, chromatography of the crude product eluting with diethyl ether and petroleum ether, 20–80 gave the product, isolated in an amount of 5.0 g, yield 89%.

$^1$H-NMR(500 MHz, CDCl3): 4.11 (s, 2H), 5.16 (s, 2H), 7.20–7.27 (m, 3H), 7.28–7.33 (m, 3H), 7.34–7.45 (m, 6H), 7.48 (s, 1H), 9.26 (s, 1H).

(c) [4-Benzyl-3-(benzyloxy)phenyl]methanol

Lithium aluminum hydride (1.56 g) was dissolved in diethyl ether (100 ml). A solution of compound (d) (6.2 g) in diethyl ether (25 ml) was added dropwise to the reaction vessel at room temperature and stirred for 1 hour. Over 30 minutes water (1.5 ml), sodium hydroxide (10%, 1.5 ml) and water (4.5 ml) were added to quench the reaction. The reaction vessel was stirred for a further 1 hour. The solid material was filtered off and the solvent evaporated. Isolated product, 5.07 g, yield 89%.

$^1$H-NMR(500 MHz, CDCl3): 4.04 (s, 2H), 4.67 (s, 2H), 5.09 (s, 2H), 6.90 (d, 1H), 7.00 (s, 1H), 7.13 (d, 1H), 7.18–7.42 (m, 10H).

(d) Methyl 4-benzyl-3-(benzyloxy)benzoate

Methyl 4-benzyl-3-hydroxybenzoate (3.95 g), benzyl bromide (3.35 g), N-ethyl-N,N-diisopropylamine (3.2 g), tetrabutylammonium iodide (0.6 g) and acetonitrile (100 ml) were added to a reaction flask. The solution was refluxed over night under a nitrogen atmosphere. The reaction had not completed so more benzyl bromide (1.0 g) and diisopropylamine (1.0 g) were added and refluxed one-night again under a nitrogen atmosphere. The solution was evaporated and the residue divided between diethyl ether and water. The organic phase was dried with sodium sulfate, filtered and the solvent evaporated to give the product (5.2 g, yield 96%).

$^1$H-NMR(500 MHz, CDCl3): 3.94 (s, 3H), 4.10 (s, 2H), 5.15 (s, 2H), 7.19–7.26 (m, 3H), 7.28–7.44 (m, 8H), 7.62–7.66 (m, 2H).

Compound methyl 4-benzyl-3-hydroxybenzoate was made according to a literature procedure, Erin Campbell, John J Martin and Edward F. Kleinman, J. Org. Chem, 61, 4806 (1996). The petroleum ether used had a boiling point of 40–60 ° C.

EXAMPLE 4

3-[3-Benzyl-4-({4-[(methylsulfonyl)oxy]phenethyl}oxy)phenyl]-2-ethoxypropanoic acid Ethyl 3-[3-benzyl-4-({4-[(methylsulfonyl)oxy]phenethyl}oxy)phenyl]-2-ethoxypropanoate—Example 5 (0.23 g; 0.42 mmole) was dissolved in THF and water (2:1), lithium hydroxide (0.014 g; 0.59 mmole) was added and the reaction mixture was stirred over night. Water was added and the THF evaporated. The remaining water was acidified with diluted hydrochloric acid and extracted with ethyl acetate. The organic phase was dried with magnesium sulfate. Evaporation gave 0.15 g (70% yield) of the product.

$^1$H-NMR (500 MHz; CDCl$_3$): δ1.15 (t, 3H), 2.90–2.97 (m, 1H), 300–3.10 (m, 3H), 3.12 (s, 3H), 3.35–3.42 (m, 1H), 3.56–3.65 (m, 1H), 3.94 (d, 2H), 4.03, q, 1H), 4.16 (t, 2H) 6.79 (d, 1H), 7.03 (d, 1H), 7.70–7.11 (m, 1H), 7.17–7.32 (m, 9H), 9.36 (bs, —COOH)

$^{13}$C-NMR (125 MHz; CDCl$_3$): δ15.3, 35.6, 36.3, 37.5, 38.2, 67.0, 68.7, 71.6, 80.0, 111.5, 122.4, 126.1, 128.5, 128.6, 129.1, 129.7, 130.9, 132.1, 138.5, 141.3, 148.1, 155.6, 176.8

EXAMPLE 4a (2S or 2R)-3-[3-Benzyl-4-({4-[(methylsulfonyl)oxy] phenethyl}oxy)phenyl]-2-ethoxypropanoic acid Ethyl (2S or 2R)-3-[3-benzyl-4-({4-[(methylsulfonyl) oxy]phenethyl}oxy)phenyl]-2-ethoxypropanoate (0.044 g; 0.084 mmole) was dissolved in THF and water (2:1), 1M lithium hydroxide (1 ml) was added and the reaction mixture was stirred overnight. Water was added and the THF evaporated. The remaining water was acidified with diluted hydrochloric acid and extracted with ethyl acetate. The organic phase was dried with magnesium sulfate. Evaporation gave 0.047 g (98% yield) of the product.

$^1$H-NMR (500 MHz; CDCl$_3$): δ1.14 (t, 3H), 2.89–2.97 (m, 1H), 3.00–3.10 (m, 3H), 3.13 (s, 3H), 3.35–3.44 (m, 1H), 3.54–3.63 (m, 1H), 3.93 (d, 2H), 4.02, q, 1H), 4.16 (t, 2H), 6.78 (d, 1H), 7.01 (d, 1H), 7.05–7.10 (m, 1H), 7.13–7.22 (m, 5H), 7.24–7.32 (m, 4H)

$^{13}$C-NMR (125 MHz; CDCl$_3$): δ15.3, 35.6, 36.3, 37.5, 38.1, 67.1, 68.6, 80.0, 111.5, 122.2, 126.1, 128.5, 128.6, 129.0, 129.1, 129.8, 130.9, 132.1, 138.5, 141.3, 148.1, 155.6, 176.8

EXAMPLE 4b (2R or 2S)-3-[3-Benzyl-4-({4-[(methylsulfonyl)oxy] phenethyl}oxy)phenyl]-2-ethoxypropanoic acid Ethyl (2R or 2S)-3-[3-benzyl-4-({4-[(methylsulfonyl) oxy]phenethyl}oxy)phenyl]-2-ethoxypropanoate (0.047 g; 0.090 mmole) was dissolved in THF and water (2:1), 1 M lithium hydroxide (1 ml) was added and the reaction mixture was stirred over night. Water was added and the THF evaporated. The remaining water was acidified with diluted hydrochloric acid and extracted with ethyl acetate. The organic phase was dried with magnesium sulfate. Evaporation gave 0.039 g (83% yield) of the product.

$^1$H-NMR (500 MHz; CDCl$_3$): δ1.15 (t, 3H), 2.90–2.97 (m, 1H), 3.01–3.10 (m, 3H), 3.13 (s, 3H), 3.35–3.43 (m, 1H), 3.56–3.65 (m, 1H), 3.93 (d, 2H), 4.03, q, 1H), 4.16 (t, 2H), 6.79 (d, 1H), 7.03 (d, 1H), 7.06–7.11 (m, 1H), 7.14–7.23 (m, 5H), 7.25–7.33 (m, 4H)

$^{13}$C-NMR (125 MHz; CDCl$_3$): δ15.3, 35.8, 36.3, 37.5, 38.2, 67.0, 68.7, 80.1, 111.5, 122.2, 126.1, 128.5, 128.6, 129.1, 129.2, 129.7, 130.9, 132.1, 138.5, 141.3, 148.1, 155.6, 176.8

EXAMPLE 5

Ethyl 3-[3-benzyl-4-({4-[(methylsulfonyl)oxy] phenethyl}oxy)phenyl]-2-ethoxypropanoate Ethyl 3-(3-benzyl-4-hydroxyphenyl)-2-ethoxypropanoate (0.50 g, 3.73 mmole) and 4-{2-[(methylsulfonyl)oxy] ethyl}phenyl methanesulfonate (2.20 g, 7.46 mmole) were dissolved in 2-butanone (20 ml). Polyethyleneglycol 400 (0.20 g) and anhydrous potassium carbonate (0.78 g, 5.59 mmole) were added the mixture. After stirring at reflux for 16 hours it was checked using HPLC whether all the starting material was consumed. The mixture was washed with water dried with magnesium sulfate and evaporated. Purification of the crude product with preparative HPLC (Kromasil C8, 10 μm, 50×500 mm) using acetonitrile (60–80%) in ammonium acetate buffer (pH 7) as mobile phase gave 0.71 g (36% yield) of the desired product $^1$H-NMR (500 MHz; CDCl$_3$): δ1.17 (t, 3H), 1.24 (t, 3H), 2.93–2.97 (m, 2H), 3.08 (t, 2H), 3.12 (s, 3H), 3.32–3.40 (m, 1H), 3.57–3.65 (m, 1H), 3.90–4.00 (m, 3H), 4.12–4.20 (m, 4H), 6.79 (d, 1H), 7.02 (d, 1H), 7.07–7.11 (m, 1H), 7.15–7.33 (m, 9H)

$^{13}$C-NMR (125 MHz; CDCl$^3$): δ14.5, 15.4, 35.6, 36.3, 37.5, 38.8, 53.8, 61.0, 66.4, 68.7, 71.3, 80.6, 111.5, 122.2, 126.1, 128.5, 128.6, 129.1, 129.5, 129.6, 130.9, 132.0, 138.5, 141.4, 148.1, 155.5, 172.8

Starting Material (a) Ethyl 3-(3-benzyl-4-hydroxyphenyl)-2-ethoxypropanoate

Compound (b) (0.88 g, 2.11 mmole) was hydrogenated in methanol (50 ml) at atmospheric pressure using Pd/C (5%) as a catalyst. The mixture was filtered through celite and evaporated in vacuo to give the desired product 0.61 g (86% yield).

$^1$H-NMR (400 MHz; CDCl$_3$): δ1.19 (t, 3H), 1.23 (t, 3H), 2.97 (d, 2H), 3.35–3.45 (m, 1H), 3.59–3.69 (m, 1H), 4.00 (s, 2H), 4.03 (t, 1H), 4.11–4.21 (m, 2H), 5.93 (bs, —OH), 6.70 (d, 1H), 6.95–7.02 (m, 2H), 7.19–7.35 (m, 5H)

$^{13}$C-NMR (100 MHz; CDCl$_3$): δ14.5, 15.3, 36.3, 38.8, 61.3, 66.5, 80.8, 115.8, 126.3, 127.4, 128.6, 128.7, 128.9, 129.1, 132.1, 140.9, 153.1, 173.3

(b) Ethyl (E)-3-[3-benzyl-4-(benzyloxy)phenyl]-2-ethoxy-2-propenoate

Compound (c) and (1,2-diethoxy-2-oxoethyl)(triphenyl) phosphonium chloride (2.89 g, 6.74 mmole) were dissolved in isopropanol (100 ml) and anhydrous potassium carbonate (1.24 g, 9.00 mmole) was added and the mixture was refluxed overnight. The precipitate was filtered off and the solvent evaporated in vacuo. Purification of the crude product with preparative HPLC (Kromasil C8, 10 μm, 50×500 mm) using acetonitrile (50–70%) in ammonium acetate buffer (pH 7) as mobile phase gave 0.88 g (46% yield) of the desired product.

$^1$H-NMR (400 MHz; CDCl$_3$): δ1.29 (t, 3H), 1.37 (t, 3H), 3.93 (q, 2H), 4.04 (s,2H), 4.29 (q, 2H), 5.11 (s, 2H), 6.90–6.95 (m, 2H), 7.18–7.41 (m, 10H), 7.62–7.66 (m, 2H)

(c) 3-Benzyl-4-(benzyloxy)benzaldehyde

Compound (d) (2.27 g, 7.46 mmole) was added to a mixture of pyridinium chlorochromate (2.41 g, 11.19 mmole) in dichloromethane (100ml). The reaction mixture was stirred for one hour after which it was quenched with ether. The precipitate was filtered off and the solvent evaporated in vacuo. Chromatography using dichloromethane as eluent gave 2.1 g (84%) of the desired product.

$^1$H-NMR (400 MHz; CDCl$_3$): δ4.07 (s, 2H), 5.17 (s, 2H), 7.03 (d, 1H), 7.18–7.42 (m, 7H), 7.71 (d, 1H), 7.73–7.78 (m, 1H), 9.87 (s, 1H)

(d) [3-Benzyl-4-(benzyloxy)phenyl]methanol

Compound (e) (2.25, 6.08 mmole) dissolved in diethyl ether (20 ml) was added dropwise to a mixture of lithium aluminum hydride (0.75 g, 19.87 mmole) in ether (100 ml). The reaction mixture was stirred one hour after which it was quenched with 5M NaOH (2 ml) and water (1 ml). The mixture was refluxed for ten minutes after which the precipitate was filtered off and the solvent was dried with magnesium sulfate and evaporated in vacuo to give the desired product 1.67 g (81% yield).

$^1$H-NMR (500 MHz; CDCl$_3$): δ1.47 (bs, —OH), 4.06 (s, 2H), 4.60 (s, 2H), 5.09 (s, 2H), 6.93 (d, 1H), 7.15–7.40 (m, 12H)

(e) Methyl 3-benzyl-4-(benzyloxy)benzoate

Methyl 3-benzyl-4-hydroxybenzoate (made according to J. Amer. Chem. Soc. (1974) 96, 2 2120–2129) was dissolved in acetonitrile (10 ml) and benzyl bromide (1.22 g, 7.12 mmole), anhydrous potassium carbonate (1.34 g, 9.70 mmole) was added. The mixture was stirred overnight, the precipitate was filtered off and the solvent was evaporated in vacuo. The residue was dissolved in ethyl acetate. The organic phase was dried with magnesium sulfate.

Evaporation gave 2.25 g (94% yield) of the desired product.

$^1$H-NMR (400 MHz; CDCl$_3$): δ3.88 (s, 2H), 4.05 (s, 2H), 5.12 (s, 2H), 6.94 (d, 1H), 7.17–7.39 (m, 10H), 7.88–7.95 (m, 2H).

EXAMPLE 5a

Ethyl (2S or 2R)-3-[3-benzyl-4-({4-[(methylsulfonyl)oxy]phenethyl}oxy)phenyl]-2-ethoxypropanoate The racemate of ethyl 3-[3-benzyl-4-({4-[(methylsulfonyl)oxy]phenethyl}oxy)phenyl]-2-ethoxypropanoate (0.40 g; 0.76 mmole) was separated using chiral preparative HPLC (Chiralpak AD 250×50 mm) using isohexane, isopropanol and methanol 92:6:2 as mobile phase giving 0.11 g (28% yield) of the enantiomeric pure (97% ee) product.

$^1$H-NMR (500 MHz; CDCl$_3$): δ1.16 (t, 3H), 1.23 (t, 3H), 2.91–2.97 (m, 2H), 3.08 (t, 2H), 3.14 (s, 3H), 3.31–3.40 (m, 1H), 3.57–3.65 (m, 1H), 3.88–4.00 (m, 3H), 4.12–4.21 (m, 4H), 6.79 (d, 1H), 7.02 (d, 1H), 7.06–7.11 (m, 1H), 7.14–7.34 (m, 9H)

$^{13}$C-NMR (125 MHz; CDCl$_3$): δ14.5, 15.4, 35.6, 36.3, 37.5, 38.8, 61.1, 66.4, 68.7, 80.7, 111.5, 122.2, 126.1, 128.5, 128.6, 129.1, 129.5, 129.6, 130.9, 132.0, 138.5, 141.4, 148.1, 155.5, 172.8

EXAMPLE 5b

Ethyl (2R or 2S)-3-[3-benzyl-4-({4-[(methylsulfonyl)oxy]phenethyl}oxy)phenyl]-2-ethoxypropanoate The racemate of ethyl 3-[3-benzyl-4-({4-[(methylsulfonyl)oxy]phenethyl}oxy)phenyl]-2-ethoxypropanoate (0.40 g; 0.76 mmole) was separated using chiral preparative HPLC (Chiralpak AD 250×50 mm) using isohexane, isopropanol and methanol 92:6:2 as mobile phase giving 0.11 g (30% yield) of the enantiomeric pure (99% ee) product.

$^1$H-NMR (500 MHz; CDCl$_3$): δ1.17 (t, 3H), 1.24 (t, 3H), 2.91–2.97 (m, 2H), 3.08 (t, 2H), 3.13 (s, 3H), 3.30–3.40 (m, 1H), 3.57–3.65 (m, 1H), 3.89–4.00 (m, 3H), 4.12–4.20 (m, 4H), 6.79 (d, 1H), 7.02 (d, 1H), 7.06–7.11 (m, 1H), 7.14–7.23 (m, 5H), 7.24–7.33 (m, 4H)

$^{13}$C-NMR (125 MHz; CDCl$_3$): δ14.5, 15.4, 35.6, 36.3, 37.5, 38.8, 61.0, 66.4, 68.7, 80.6, 111.5, 122.2, 126.1, 128.5, 128.6, 129.1, 129.5, 129.6, 130.9, 132.0, 138.5, 141.4, 148.1, 155.5, 172.8

EXAMPLE 6

3-[3-tert-Butyl-4-(2-{4-[(methylsulfonyl)oxy]phenyl}ethoxy)phenyl]-2-ethoxypropanoic acid Ethyl 3-[3-tert-butyl-4-(2-{4-[(methylsulfonyl)oxy]phenyl}ethoxy)phenyl]-2-ethoxypropanoate (0.025 g; 0.050 mmole) was dissolved in THF and water (2:1), 0.1 M lithium hydroxide (2 ml) was added and the reaction mixture was stirred over night. Water was added and the THF evaporated. The remaining water was acidified with diluted hydrochloric acid and extracted with ethyl acetate. The organic phase was dried with magnesium sulfate. Evaporation gave 0.019 g (80% yield) of the product.

$^1$H-NMR (500 MHz; CDCl$_3$): δ1.20 (t, 3H), 1.31 (s, 9H), 2.94–3.00 (m, 1H), 3.05–3.10 (m, 1H), 3.14 (s, 3H), 3.20 (t, 2H), 3.40–3.48 (m, 1H), 3.59–3.67 (m, 1H), 4.05 (dd, 1), 4.24 (t, 2H), 6.80 (d, 1H), 7.06 (dd, 1H), 7.17 (d, 1H), 7.25–7.29 (m, 2H), 7.38 (d, 2H)

$^{13}$C-NMR (125 MHz; CDCl$_3$): δ15.4, 30.0, 35.0, 35.7, 37.5, 38.4, 67.1, 68.6, 80.2, 112.0, 122.3, 128.0, 128.4, 128.6, 130.9, 138.4, 148.2, 156.6, 173.0

EXAMPLE 7

Ethyl 3-[3-tert-butyl-4-(2-{4-[(methylsulfonyl)oxy]phenyl}ethoxy)phenyl]-2-ethoxypropanoate Ethyl 3-(3-tert-butyl-4-hydroxyphenyl)-2-ethoxypropanoate (0.15 g, 0.44 mmole) and 4-{2-[(methylsulfonyl)oxy]ethyl}phenyl methanesulfonate (0.26 g, 0.89 mmole) were dissolved in 2-butanone (4 ml). Polyethyleneglycol 400 (0.05 g) and anhydrous potassium carbonate (0.092 g, 0.67 mmole) were added the mixture. After stirring at reflux for 16 hours it was checked using HPLC whether all the starting material was consumed. The mixture was washed with water dried with magnesium sulfate and evaporated. Purification of the crude product with preparative HPLC (Kromasil C8, 7 μm, 50×250 mm) using actonitrile(40–80%) in ammonium acetate buffer (pH 7) as mobile phase gave 0.048 g (22% yield) of the desired product $^1$H-NMR (300 MHz; CDCl$_3$): δ1.18 (t, 3H), 1.24 (t, 3H), 1.30 (s, 9H), 2.94 (d, 2H), 3.12 (t, 3H), 3.18 (t, 2H), 3.30–3.42 (m, 1H), 3,56–3.67 (m, 1H), 3.97 (t, 1H), 4.17 (t, 2H), 4.22 (t, 2H), 6.77 (d, 1H), 7.04 (dd, 1H), 7.15 (d, 1H), 7.23–7.29 (m, 2H), 7.34–7.40 (m, 2H)

$^{13}$C-NMR (75 MHz; CDCl$_3$): δ14.6, 15.5, 30.1, 35.1, 35.8, 37.5, 39.1, 61.1, 66.5, 68.8, 80.8, 111.9, 122.2, 127.7, 128.3, 129.1, 130.8, 137.8, 138.4, 148.1, 156.4, 172.9

Starting Material Ethyl 3-(3-tert-butyl-4-hydroxyphenyl)-2-ethoxypropanoate

Ethyl (2Z)-3-[4-(benzyloxy)-3-tert-butylphenyl]-2-ethoxyacrylate (0.24 g, 0.56 mmole) was hydrogenated in ethylacetate (10 ml) at atmospheric pressure using Pd/C (5%) as a catalyst. The mixture was filtered through celite and evaporated in vacuo gave 0.15 g (81% yield) of the desired product $^1$H-NMR (400 MHz; CDCl$_3$): δ1.19 (t, 3H), 1.24 (t, 3H), 1.41 (s, 9H), 2.95 (d, 2H), 3.33–3.43 (m, 1H), 3.58–3.67 (m, 1H), 4.00 (t, 1H), 4.11–4.22 (m, 2H), 5.30 (—OH), 6.59 (d, 2H), 6.94 (dd, 1H), 7.13 (d, 1H)

Ethyl (2Z)-3-[4-(benzyloxy)-3-tert-butylphenyl]-2-ethoxyacrylate 4-(Benzyloxy)-2-tert-butylbenzaldehyde (0.66 g; 2.44 mmole) and ethyl ethoxyacetate (0.39 g; 2.93 mmole) were dissolved in dry tetrahydrofuran (10 ml) and cooled to −20° C. Potassium tert-butoxide (0.33 g; 2.93 mmole) dissolved in dry tetrahydrofuran (1 ml) was slowly added and the reaction was stirred overnight at −20° C. The reaction was quenched with acetic acid (0.19 g; 3.18 mmole). The crude product was isolated, redissolved in toluene and refluxed over night with p-toluenesulfonic acid (0.05 g; 0.25 mmole) in a Dean-Stark apparatus to separate the water. The solution was cooled, washed with sodium hydrogen carbonate, dried with magnesium sulfate and evaporated. Purification of the crude product with preparative HPLC (Kromasil C8, 7 μm, 50×250 mm) using acetronitrile (50–100%) in ammonium acetate buffer (pH 7) as mobile phase gave 0.26 g (25% yield) of ethyl (2Z)-3-[4-(benzyloxy)-3-tert-butylphenyl]-2-ethoxyacrylate.

$^1$H-NMR (500 MHz; CDCl$_3$): δ1.40 (t, 3H), 1.42 (t, 3H), 1.45 (s, 9H), 4.01 (q, 2H) 4.32 (q, 2H), 5.18 (s, 2H), 6.96 (d, 1H), 7.01 (s, 1H), 7.33–7.51 (m, 5H), 7.66 (dd, 1H), 7.85 (d, 1H)

EXAMPLE 8

3-[3-[(tert-Butoxycarbonyl)amino]-4-(2-{4-[(methylsulfonyl)oxy]phenyl}ethoxy)phenyl]-2-ethoxypropanoic acid Ethyl 3-[3-[(tert-butoxycarbonyl)amino]-4-(2-{4-[(methylsulfonyl)oxy]phenyl}ethoxy)phenyl]-2-ethoxypropanoate (0.036 g; 0.100 mmole) was dissolved in THF and water (2:1), 0.1 M lithium hydroxide (1 ml) was added and the reaction mixture was stirred over night. Water was added and the THF evaporated. The remaining water was acidified with diluted hydrochloric acid and extracted with ethyl acetate. The organic phase was dried with magnesium sulfate. Evaporation gave 0.012 g (52% yield) of the product.

$^1$H-NMR (400 MHz; CDCl$_3$): δ1.19 (t, 3H), 1.55 (s, 9H), 2.90–2.98 (m, 1H), 3.05–3.11 (m, 1H), 3.12–3.17 (m, 5H), 3.42–3.52 (m, 1H), 3.56–3.65 (m, 1H), 4.08 (q, 1H), 4.21 (t, 2H), 6.74 (d, 1H), 6.83 (dd, 1H), 6.92 (s, 1H), 7.24–7.29 (m, 2H), 7.31 (m, 2H), 7.99 (—NH)

EXAMPLE 9

Ethyl 3-[3-[(tert-butoxycarbonyl)amino]-4-(2-{4-[(methylsulfonyl)oxy]phenyl}ethoxy)phenyl]-2-ethoxypropanoate Ethyl 3-{3-[(tert-butoxycarbonyl)amino]-4-hydroxyphenyl}-2-ethoxypropanoate (0.16 g, 0.44 mmole) and 4-{2-[(methylsulfonyl)oxy]ethyl}phenyl methanesulfonate (0.26 g, 0.88 mmole) were dissolved in 2-butanone (10 ml). Polyethyleneglycol 400 (0.05 g) and anhydrous potassium carbonate (0.092 g, 0.66 mmole) were added the mixture. After stirring at reflux for 16 hours it was checked with using HPLC whether all the starting material was consumed. The mixture was washed with water dried with magnesium sulfate and evaporated. Purification of the crude product with preparative HPLC (Kromasil C8, 7 µm, 50×250 mm) using actonitrile(60–80%) in ammonium acetate buffer (pH 7) as mobile phase gave 0.052 g (21% yield) of the desired product $^1$H-NMR (500 MHz; CDCl$_3$): δ1.17 (t, 3H), 1.24 (t, 3H), 2.93–2.97 (m, 2H), 3.08 (t, 2H), 3.12 (s, 3H), 3.32–3.40 (m, 1H), 3.57–3.65 (m, 1H), 3.90–4.00 (m, 3H), 4.12–4.20 (m, 4H), 6.79 (d, 1H), 7.02 (d, 1H), 7.07–7.11 (m, 1H), 7.15–7.33 (m, 9H)

$^{13}$C-NMR (125 MHz; CDCl$_3$): δ14.5, 15.4, 28.7, 35.4, 37.6, 39.2, 61.1, 66.4, 69.1, 80.5, 80.6, 111.1, 119.2, 122.5, 123.7, 128.3, 130.5, 130.8, 137.9, 145.4, 148.3, 152.9, 172.8

Starting Material—Ethyl 3-{3-[(tert-butoxycarbonyl)amino]-4-hydroxyphenyl}-2-ethoxypropanoate Ethyl 3-(3-amino-4-hydroxyphenyl)-2-ethoxypropanoate (0.25 g, 0.92 mmole) was dissolved in THF (10 ml) and cooled to a 0° C. Di-tert-butyldicarbonate (0.22 g, 1.01 mmole) was added and the reaction mixture was allowed to reach room temperature, then stirred at room temperature over night. Water was added and the THF evaporated water phase was extracted with ethyl acetate. The organic phase was dried with magnesium sulfate. Chromatography of the crude material from methanol and methylene chloride, gradient elution from 0–4% gave 0.16 g (46% yield) of the product.

$^1$H-NMR (500 MHz; CDCl$_3$): δ1.21 (t, 3H), 1.27 (t, 3H), 1.57 (s, 9H), 2.90–3.00 (m, 2H) 3.34–3.44 (m, 1H), 3.60–3.68 (m, 1H), 4.01 (t, 1H), 4.20 (q, 2H), 6.74 (s, 1H),.6.85–6.95 (dd, 2H), 7.09 (s, 1H), 8.07 (—NH)

Ethyl 3-(3-amino-4-hydroxyphenyl)-2-ethoxypropanoate

Ethyl (2Z)-3-[4-(benzyloxy)-3-nitrophenyl]-2-ethoxyacrylate (0.83 g, 1.57 mmole) was hydrogenated in ethylacetate (10 ml) at atmospheric pressure using Pd/C (5%) as a catalyst. The mixture was filtered through celite and evaporated in vacuo. Purification of the crude product with preparative HPLC (Kromasil C8, 7 µm, 50×250 mm) using actonitrile(0–60%) in ammonium acetate buffer (pH 7) as mobile phase gave 0.052 g (13% yield) of the desired product.

$^1$H-NMR (400 MHz; CDCl$_3$): δ1.17 (t, 3H), 2.87 (d, 2H), 3.33–3.43 (m, 1H), 3.53–3.66 (m, 1H), 4.00 (t, 1H), 4.10–4.22 (m, 1H), 4.58 (—NH2), 6.47–6.52 (m, 1H), 6.56–6.68 (m, 2H)

Ethyl (2Z)-3-[4-(benzyloxy)-3-nitrophenyl]-2-ethoxyacrylate 4-(Benzyloxy)-3-nitrobenzaldehyde (4.12 g; 14.4 mmole) and ethyl ethoxyacetate (2.29 g; 17.3 mmole) were dissolved in dry tetrahydrofuran (20 ml) and cooled to −20° C. Potassium tert-butoxide (1.94 g; 17.3 mmole) dissolved in dry tetrahydrofuran (10 ml) was slowly added and the reaction was stirred overnight at −20° C. The reaction was quenched with acetic acid (1.3 g; 21.7 mmole). The crude product was isolated, redissolved in toluene and refluxed over night with p-toluenesulfonic acid (0.25 g; 1.44 mmole) in a Dean-Stark apparatus to separate the water. The solution was cooled, washed with sodium hydrogen carbonate, dried with magnesium sulfate and evaporated. Chromatography of the crude material from methylene chloride gave 0.85 g (11% yield) of ethyl (2Z)-3-[4-(benzyloxy)-3-nitrophenyl]-2-ethoxyacrylate.

$^1$H-NMR (500 MHz; CDCl$_3$): δ1.25 (t, 3H), 1.30 (t, 3H), 3.56–3.70 (m, 1H), 3.70–3.85 (m, 1H), 4.20–4.32 (m, 2H), 4.93 (s, 1H), 5.39 (s, 2H), 7.18 (d, 1H), 7.35–7.50 (m, 5H), 8.31 (dd, 1H), 8.65 (d, 1H)

EXAMPLE 10

2-Ethoxy-3-{4-[2-(4-hydroxyphenyl)ethoxy]-3-methylphenyl}propanoic acid

Ethyl 2-ethoxy-3-[3-methyl-4-(2-{4-[(methylsulfonyl)oxy]phenyl}ethoxy)phenyl]propanoate (0.150 g; 0.330 mmole) was dissolved in THF. 5M sodium hydroxide (10 eqv) was added and the reaction mixture was stirred over night. Water was added and the THF evaporated. The remaining water was acidified with diluted hydrochloric acid and extracted with ethyl acetate. The organic phase was dried with magnesium sulfate. Purification of the crude product with preparative HPLC (Kromasil C8, 7 µm, 50×250 mm) using acetronitrile (20–100%) in ammonium acetate buffer (pH 7) as mobil phase gave 0.012 g (8% yield) of the desired product.

$^1$H-NMR (500 MHz; CDCl$_3$): δ1.21 (t, 3H), 2.20 (s, 3H), 2.91–2.98 (m, 1H), 3.02–3.09 (m, 3H), 3.43–3.51 (m, 1H), 3.59–3.67 (m, 1H), 4.08 (q, 1H), 4.13 (t, 2H), 6.73 (d, 1H), 6.81 (d, 2H), 7.00–7.05 (m, 2H), 7.16–7.20 (d, 2H)

EXAMPLE 11

Ethyl 2-ethoxy-3-[3-methyl-4-(2-{4-[(methylsulfonyl)oxy]phenyl}ethoxy)phenyl]propanoate Ethyl 2-ethoxy-3-(4-hydroxy-3-methylphenyl)propanoate (0.27 g, 1.05 mmole) and 4-{2-[(methylsulfonyl)oxy]ethyl}phenyl methanesulfonate (0.62 g, 2.11 mmole) were dissolved in 2-butanone (10 ml). Polyethyleneglycol 400 (0.20 g) and anhydrous potassium carbonate (0.22 g, 1.58 mmole) were added the mixture. After stirring at reflux for 16 hours it was checked with using HPLC whether all the starting material was consumed. The mixture was washed with water dried with magnesium sulfate and evaporated. Purification of the crude product with preparative HPLC (Kromasil C8, 7 µm, 50×250 mm) using actonitrile (60–80%) in ammonium acetate buffer (pH 7) as mobile phase gave 0.28 g (54% yield) of the desired product.

$^1$H-NMR (400 MHz; CDCl$_3$): δ1.18 (t, 3H), 1.24 (t, 3H), 2.16 (s, 3H), 2.92 (d, 2H), 3.08–3.14 (m, 5H), 3.32–3.42 (m, 1H), 3.55–3.65 (m, 1H), 3,98 (t, 3H), 4.10–4.21 (m, 4H), 6.68–6.73 (m, 1H), 6.98–7.03 (m, 2H), 7.19–7.26 (m, 2H), 7.32–7.38 (m, 2H)

$^{13}$C-NMR (100 MHz; CDCl$_3$): δ14.5, 15.4, 16.5, 35.6, 37.5, 38.8, 61.0, 66.4, 68.5, 80.7, 111.0, 122.1, 126.7, 127.8, 129.3, 130.9, 132.1, 138.6, 148.2, 155.8, 172.9

Starting Material—Ethyl 2-ethoxy-3-(4-hydroxy-3-methylphenyl)propanoate

Ethyl (2Z)-3-[4-(benzyloxy)-3-methylphenyl]-2-ethoxyacrylate (0.83 g, 2.40 mmole) was hydrogenated in methanol (25 ml) at atmospheric pressure using Pd/C (5%) as a catalyst. The mixture was filtered through celite and evaporated in vacuo to give the desired product 0.54 g (88% yield).

$^1$H-NMR (400 MHz; CDCl$_3$): δ1.19 (t, 3H), 1.25 (t, 3H), 2.24 (s, 3H), 2.93 (d, 2H), 3.33–3.42 (m, 1H), 3.57–3.67 (m, 1H), 3.98 (t, 1H), 4.18 (q, 2H), 6.69 (d, 1H), 6.96 (dd, 1H), 7.01 (s, 1H)

Ethyl (2Z)-3-[4-(benzyloxy)-3-methylphenyl]-2-ethoxyacrylate 4-(Benzyloxy)-3-methylbenzaldehyde (2.36 g; 10.2 mmole) and ethyl ethoxyacetate (1.62 g; 12.3 mmole) were dissolved in dry THF (10 ml) and cooled to −20° C. Potassium tert-butoxide (1.38 g; 12.3 mmole) dissolved in dry tetrahydrofuran (1 ml) was slowly added and the reaction was stirred over night at −20° C. The reaction was quenched with acetic acid (0.80 g; 13.3 mmole). The crude product was isolated, redissolved in toluene and refluxed overnight with p-toluenesulfonic acid (0.18 g; 1.0 mmole) in a Dean-Stark apparatus to separate the water. The solution was cooled, washed with sodium hydrogen carbonate, dried with magnesium sulfate and evaporated. Purification of the crude product with preparative HPLC (Kromasil C8, 10 μm, 50×500 mm) using acetonitrile (50–100%) in ammonium acetate buffer (pH 7) as mobile phase gave 0.86 g (25% yield) of ethyl (2Z)-3-[4-(benzyloxy)-3-methylphenyl]-2-ethoxyacrylate.

$^1$H-NMR (500 MHz; CDCl$_3$): δ1.41 (t, 3H), 1.43 (t, 3H), 2.34 (s, 3H), 4.03 (q, 2H), 4.34 (q, 2H), 5.17 (s, 2H), 6.92 (d, 1H), 7.00 (s, 1H), 7.36–7.52 (m, 5H), 7.66–7.71 (m, 2H)

EXAMPLE 12

3-[3-Benzyl-4-(2-{4-[(tert-butoxycarbonyl)amino]phenyl}ethoxy)phenyl]-2-ethoxypropanoic acid Ethyl 3-[3-benzyl-4-(2-{4-[(tert-butoxycarbonyl)amino]phenyl}ethoxy)phenyl]-2-ethoxypropanoate (0.3 g, 0.5 mmol) and lithium hydroxide (0.015 g, 0.6 mmol) was added to a mixture of THF (10 ml), ethanol (2 ml) and water (2 ml). After stirring in room temperature for 5 h the mixture was acidified to pH 3 with saturated potassium hydrogen sulphate. Water was added and the mixture was extracted with ethylacetate. The organic layer was separated and evaporated. The residue was purified on silica gel using isooctane/ethylacetate/methanol 10:10:1. This yielded 70 mg (0.1 mmol) of the title product.

$^1$H-NMR (400 MHz, CDCl$_3$): δ1.12 (t, 3H), 1.53 (s, 9H), 2.9 (m, 1H), 3.02 (m, 3H), 3.35 (m, 1H), 3.57 (m, 1H), 3.92 (m, 1H) 4.0 (m, 2H), 4.11 (t, 2H), 6.58 (bs, 2H), 6.74 (d, 1H), 7.0 (s, 1H), 7.04 (d, 1H), 7.13–7.31 (m, 9H)

$^{13}$C-NMR (400 MHz, CDCl$_3$): δ15.2, 28.6, 35.5, 36.2, 38.1, 67.0, 69.1, 80.1, 125.9, 128.4, 128.8, 129.1, 129.7, 129.9, 131.8, 133.5, 136.9, 141.3, 175.5

EXAMPLE 13

Ethyl 3-[3-benzyl-4-(2-{4-[(tert-butoxycarbonyl)amino]phenyl}ethoxy)phenyl]-2-ethoxypropanoate Ethyl 3-(3-benzyl-4-hydroxyphenyl)-2-ethoxypropanoate (2 g, 6 mmol), 2-{4-[(tert-butoxycarbonyl}amino]phenyl}ethyl 4-methylbenzenesulfonate (3.6 g, 9 mmol); was solved in 2-butanone (30 ml). PEG-400 (0.8 g) and potassium carbonate (2.6 g, 19 mmol) was added and the mixture was refluxed for 8 h. Water was added, the organic layer separated and evaporated. The residue was purified on silica gel using isooctane/ethylacetate 2:1 which yielded 0.38 g (0.7 mmol) of the title product.

$^1$H-NMR (600 MHz, CDCl$_3$): δ1.12 (t, 3H), 1.18 (t, 3H), 1.5 (s, 9H), 2.88 (m, 2H), 2.98 (m, H), 3.31 (m, 1H), 3.55 (m, 1H), 3.9 (m, 3H), 4.09 (m, 3H), 4.26 (m, 1H), 6.45 (bs, 1H), 6.73 (d, 1H), 6.96 (s, 1H), 7.04 (d, 1H), 7.14–7.32 (m, 9H)

$^{13}$C-NMR (600 MHz, CDCl$_3$): δ14.4, 15.3, 25.7, 28.6, 30.3, 34.6, 35.5, 36.2, 38.7, 61.0, 66.4, 69.1, 80.6, 111.4, 118.9, 125.9, 127.4, 128.4, 129.1, 129,3, 129.6, 129.7, 131.8, 133.4, 136.9, 141.4, 155.5, 172.8

EXAMPLES 14

2-Ethoxy-3-[4-methoxy-3-(2-{4-[(methylsulfonyl)oxy]phenyl}ethoxy)phenyl]propanoic acid Ethyl 2-ethoxy-3-[4-methoxy-3-(2-{4-[(methylsulfonyl)oxy]phenyl}ethoxy)phenyl]propanoate (0.483 g, 1.04 mmol) was dissolved in THF (5.0 ml) in a round bottom flask. LiOH (0.027 g, 1.14 mmol) was dissolved in H$_2$O (2.0 ml) and the solution was added dropwise at 0° C. to the flask. After stirring 24 hours at room temperature the reaction mixture was acidified (2 M HCl, 3 ml), the layers were separated and the water layer was extracted with EtOAc (3×30 ml). The combined organic extracts were dried (MgSO$_4$), filtered and concentrated under reduced pressure to yield a colourless oil (0.286 g). The oil was dissolved in EtOAc, NaHCO3 (aq,sat) (30 mL) was added, the layers were separated, the water layer was acidified (2 M HCl, 20 mL) and extracted with EtOAc (3×30 mL). To get product into the organic layer CH$_2$Cl$_2$ was added, the water layer was concentrated under reduced pressure, CH$_3$OH (20 ml) was added, concentrated CH$_2$Cl$_2$ (20 ml) was added, H$_2$O (10 ml) and CH$_2$Cl$_2$ (20 ml) were added. The layers were separated and the organic layer was concentrated under reduced pressure to yield a pale grey brownish oil (0.217 g). NMR showed both product and dimesylate impurity. The oil was dissolved in a small amount of EtOAc (5 ml). NaHCO$_3$ (10 ml) was added. The layers were separated, the water layer was acidified (2M HCl, 15 ml) and extracted with EtOAc (3×20 ml). The combined organic extracts were dried (MgSO$_4$), filtered and concentrated under reduced pressure to yield product as a pale yellow oil (0.046 g, 10%).

$^1$H-NMR(500 MHz, CDCl$_3$): 1.18 (t, 3H), 2.93 (dd, 1H), 3.06 (dd, 1H), 3.14 (s, 3H), 3.16 (t, 2H), 3.45 (m, 1H), 3.61 (m, 1H), 3.85 (s, 3H), 4.05 (m, 1H), 4.21 (t, 2H), 6.78–6.83 (m, 3H), 7.21–7.29 (m, 3H), 7.34–7.39 (m, 2H).

Starting Material—Ethyl 2-ethoxy-3-[4-methoxy-3-(2-{4-[(methylsulfonyl)oxy]phenyl}ethoxy)phenyl]propanoate K$_2$CO$_3$ (0.352 g, 2.55 mmol) was added to a solution of 4-{2-[(methylsulfonyl)oxy]ethyl}phenyl methanesulfonate (0.625 g, 2.12 mmol) in CH$_3$CN (2 ml) at 60° C. under Ar. Ethyl 2-ethoxy-3-(3-hydroxy-4-methoxyphenyl)propanoate (0.570 g, 2.12 mmol) dissolved in CH$_3$CN (0.5 ml) was added dropwise. The reaction mixture was stirred under Ar at 60° C. for 26 hours. The orange-red slurry was filtered and concentrated under reduced pressure to yield a red crude oil (0.896 g). After storage in the freezer for three days the oil was dissolved in a very small amount of CH$_2$Cl$_2$ and purified using flash-chromatography (heptan/EtOAc, 1:0–1:1). Obtained 0.517 g of unpure product, some 4-{2-[(methylsulfonyl)oxy]ethyl}phenyl methanesulfonate remained.

$^1$H-NMR(400 MHz, CDCl$_3$): 1.16 (t, 3H), 1.24 (t, 3H), 2.93 (m, 2H), 3.14 (s, 3H), 3.16 (m, 2H), 3.35 (m, 1H), 3.61 (m, 1H), 3.84 (s, 3H), 3.97 (m, 1H), 4.14–4.23 (m, 4H), 6.81 (m, 3H) 7.24 (d, 2H), 7.37 (d, 2H).

EXAMPLE 15

2-Ethoxy-3-[3-methoxy-4-(2-{4-[(methylsulfonyl)oxy]phenyl}ethoxy)phenyl]propanoic acid The crude material from the synthesis of ethyl 2-ethoxy-3-[3-methoxy-4-(2-{4-[(methylsulfonyl)oxy]phenyl}ethoxy)phenyl]propanoate (0.365 g, 0.78 mmol) was dissolved in THF (3.5 ml), and a solution of LiOH (0.021 g, 0.86 mmol) in H$_2$O (1.5 ml) was added dropwise at 0° C. After 24 hours stirring at room temperature NaHCO$_3$ (aq,sat) (5 ml) was added. The two phases separated and the water layer was washed with EtOAc (3×30 ml), acidified (2 M HCl, 5 ml) and extracted with EtOAc (3×30 ml). The combined organic phases were dried (MgSO$_4$), filtered and concentrated under reduced pressure to yield a colourless oil (0.306, 89%).

$^1$H-NMR(500 MHz, CDCl$_3$): 1.19 (t, 3H), 2.96 (dd, 1H), 3.07 (dd, 1H), 3.14 (s, 3H), 3.15 (t, 2H), 3.43 (m, 1H), 3.64 (m, 1H), 3.85 (s, 3H), 4.06 (m, 1H), 4.20 (m, 1H), 6.78 (m, 2H), 6.83 (m, 1H), 7.23 (d, 2H), 7.36 (d, 2H).

Starting Material—Ethyl 2-ethoxy-3-[3-methoxy-4-(2-{4-[(methylsulfonyl)oxy]phenyl}ethoxy)phenyl]propanoate K$_2$CO$_3$ (0.352 g, 2.55 mmol) was added to a solution of 4-{2-[(methylsulfonyl)oxy]ethyl}phenyl methanesulfonate (0.625 g, 2.12 mmol) in CH$_3$CN (2 ml) at 60° C. under Ar. Ethyl 2-ethoxy-3-(4-hydroxy-3-methoxyphenyl)propanoate (0.570 g, 2.12 mmol) dissolved in CH$_3$CN (0.5 mL) was added dropwise. The reaction mixture was stirred under Ar at 60° C. for 26 hours. The pale yellow slurry was filtered and concentrated under reduced pressure to yield a yellow crude oil (1.008 g). After storage in the freezer for three days the oil was dissolved in a very small amount of CH$_2$Cl$_2$ and purified using flash chromatography (heptane/EtOAc, 1:0–1:1). Isolated a colourless oil (0.363 g), with some 4-{2-[(methylsulfonyl)oxy]ethyl}phenyl methanesulfonate left.

$^1$H-NMR(400 MHz, CDCl$_3$): 1.16 (t, 3H), 1.23 (t, 3H), 2.94 (m, 2H), 3.11 (s, 3H), 3.12 (m, 2H), 3.35 (m, 1H), 3.60 (m, 1H), 3.83 (s, 3H), 3.97 (m, 1H), 4.14–4.20 (m, 4H), 6.76 (m, 2H), 6.82 (m, 1H), 7.91 (d, 2H), 7.34 (d, 2H).

What is claimed is:

1. A compound or, as appropriate, a stereoisomer or optical isomer or racemate thereof, or a pharmaceutically acceptable salt and/or solvate of the compound, stereoisomer, optical isomer or racemate, selected from:

3[4-Benzyl-3-({4-[(methylsulfonyl)oxy]phenethyl}oxy)phenyl]-2-ethoxypropanoic acid;

Ethyl 3-[4-benzyl-3-({4-[(methylsulfonyl)oxy]phenethyl}oxy)phenyl]-2-ethoxypropanoate;

Isopropyl 3-[4-benzyl-3-({4-[(methylsulfonyl)oxy]phenethyl}oxy)phenyl]-2-ethoxypropanoate;

3-[3-Benzyl-4-{(4-[(methylsulfonyl)oxy}phenethyl]oxy)phenyl]-2-ethoxypropanoate acid;

(2S)-3-[3-Benzyl-4-({4-[(methylsulfonyl)oxy]phenethyl}oxy)phenyl]-2-ethoxypropanoic acid;

(2R)-3-[3-Benzyl-4-({4-[(methylsulfonyl)oxy]phenethyl}oxy)phenyl]-2-ethoxypropanoic acid;

Ethyl 3-[3-benzyl-4-({4-[(methylsulfonyl)oxy]phenethyl}oxy)phenyl]-2-ethoxypropanoate;

Ethyl (2S)-3-[3-benzyl-4-({4-[(methylsulfonyl)oxy]phenethyl}oxy)phenyl]-2-ethoxypropanoate;

Ethyl (2R)-3-[3-benzyl-4-({4-[(methylsulfonyl)oxy]phenethyl}oxy)phenyl]-2-ethoxypropanoate;

3-[(3-tert-Butyl-4-(2-{4-[(methylsulfonyl)oxy]phenyl}ethoxy)phenyl]-2-ethoxypropanoic acid;

Ethyl 3-[3-tert-butyl-4-(2-{4-[(methylsulfonyl)oxy]phenyl)ethoxy}phenyl]-2-ethoxypropanoate;

3-[3-[(tert-Butoxycarbonyl)amino]4-(2-{4-[(methylsulfonyl)oxy]phenyl}ethoxy(phenyl]-2-ethoxypropanoic acid;

Ethyl 3-[3-[(tert-butoxycarbonyl)amino]-4-(2-{4-[(methylsulfonyl)oxy]phenyl}ethoxy)phenyl]-2-ethoxypropanoate;

2-Ethoxy-3-{4-[2-(4-hydroxyphenyl)ethoxy]-3-methylphenyl}propanoic acid;

Ethyl 2-ethoxy-3-[3-methyl-4-(2-{4-[(methylsulfonyl)oxy]phenyl}ethoxy)phenyl]propanoate;

3-[3-Benzyl-4-(2-{4-[(tert-butoxycarbonyl)amino]phenyl}ethoxy)phenyl]2-ethoxypropanoic acid;

Ethyl 3-[3-benzyl-4-(2-{4-[(tert-butoxycarbonyl)amino]phenyl}ethoxy)phenyl]-2-ethoxypropanoate;

2-Ethoxy-3-[4-methoxy-3-(2-{4-[(methylsulfonyl)oxy]phenyl}ethoxy)phenyl]propanoic acid; or 2-Ethoxy-3-[3-methoxy-4-(2-{4-[(methylsufonyl)oxy)]phenyl}ethoxy)phenyl]propanoic acid.

2. A pharmaceutical formulation comprising a compound according to claim 1 and a pharmaceutically acceptable adjuvant, diluent or carrier.

3. A method for treatment of conditions associated with a patient having reduced sensitivity to insulin, which comprises administering a compound according to claim 1 to a patient in need of such treatment.

* * * * *

UNITED STATES PATENT AND TRADEMARK OFFICE
CERTIFICATE OF CORRECTION

PATENT NO. : 6,750,252 B2  
DATED : June 15, 2004  
INVENTOR(S) : Boije et al.

Page 1 of 1

It is certified that error appears in the above-identified patent and that said Letters Patent is hereby corrected as shown below:

Title page,  
Item [87], PCT. Pub. Date, should read -- June 7, 2001 --.

Column 7,  
Lines 32-37, that portion of the formula reading "$R^f$" should read -- $R^r$ --  
Line 39, "$R^f$" should read -- $R^r$ --

Column 28,  
Lines 3-4, Compound name should read: -- 3-[3-Benzyl-4-({4-[(methylsulfonyl)oxy]phenethyl}oxy)phenyl]-2-ethoxypropanoic acid --  
Line 38, "(methylsufonyl)" should read -- (methylsulfonyl) --

Signed and Sealed this

Eighteenth Day of January, 2005

JON W. DUDAS  
*Director of the United States Patent and Trademark Office*